United States Patent
Sasaki et al.

(10) Patent No.: US 11,222,400 B2
(45) Date of Patent: Jan. 11, 2022

(54) IMAGE PROCESSING DEVICE, MICROSCOPE SYSTEM, IMAGE PROCESSING METHOD, AND COMPUTER PROGRAM FOR DISPLAYING MAGNIFIED IMAGES FROM DIFFERENT OBSERVATION DIRECTIONS

(71) Applicant: NIKON CORPORATION, Tokyo (JP)

(72) Inventors: Yutaka Sasaki, Yokohama (JP); Toshiya Okabe, Yokohama (JP); Ichiro Sase, Yokohama (JP); Ryosuke Komatsu, Yokohama (JP); Johana Trojanova, Prague (CZ); Miroslav Svoboda, Jílové u Prahy (CZ)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 16/464,079

(22) PCT Filed: Nov. 24, 2016

(86) PCT No.: PCT/JP2016/084865
§ 371 (c)(1),
(2) Date: May 24, 2019

(87) PCT Pub. No.: WO2018/096638
PCT Pub. Date: May 31, 2018

(65) Prior Publication Data
US 2019/0295219 A1    Sep. 26, 2019

Related U.S. Application Data

(63) Continuation of application No. PCT/JP2016/084865, filed on Nov. 24, 2016.

(51) Int. Cl.
*G06T 3/40*    (2006.01)
*G06T 5/00*    (2006.01)
(Continued)

(52) U.S. Cl.
CPC .......... *G06T 3/40* (2013.01); *A61B 6/03* (2013.01); *G02B 21/00* (2013.01); *G06F 3/0484* (2013.01);
(Continued)

(58) Field of Classification Search
None
See application file for complete search history.

(56) References Cited

U.S. PATENT DOCUMENTS

2010/0253774 A1   10/2010  Yoshioka et al.
2011/0129135 A1*   6/2011  Mizutani ............... G06T 11/60
                                                      382/128
(Continued)

FOREIGN PATENT DOCUMENTS

JP    2006-49155 A     2/2006
JP    2010-243597 A   10/2010
(Continued)

OTHER PUBLICATIONS

Feb. 7, 2017 Written Opinion issued in International Patent Application No. PCT/JP2016/084865.
(Continued)

*Primary Examiner* — Jeffrey J Chow
(74) *Attorney, Agent, or Firm* — Oliff PLC

(57) ABSTRACT

An image processor including: an accepting unit that accepts designation of at least part of three dimensional image of a microscope, and an image generator that generates image data for displaying, on a display, a first magnified image which corresponds to the part of the three dimensional image designated and a second magnified image which corresponds to the part of the three dimensional image designated and which is different from the first magnified image.

32 Claims, 16 Drawing Sheets

(51) Int. Cl.
    *A61B 6/03*     (2006.01)
    *H04N 7/18*     (2006.01)
    *G06F 3/0484*     (2013.01)
    *G02B 21/00*     (2006.01)
    *G06T 1/00*     (2006.01)

(52) U.S. Cl.
    CPC ............... *G06T 1/00* (2013.01); *G06T 5/009* (2013.01); *H04N 7/18* (2013.01); *G06T 2200/24* (2013.01); *G06T 2207/10056* (2013.01); *G06T 2207/20208* (2013.01)

(56) References Cited

U.S. PATENT DOCUMENTS

| | | |
|---|---|---|
| 2012/0070039 A1 | 3/2012 | Morimoto et al. |
| 2013/0229493 A1* | 9/2013 | Ikuta ............... G02B 21/0076 348/46 |
| 2014/0184778 A1 | 7/2014 | Takayama |
| 2014/0301665 A1* | 10/2014 | Saito ..................... G16H 30/20 382/299 |
| 2014/0323330 A1* | 10/2014 | Bergo ............... G01N 33/54373 506/9 |
| 2017/0251191 A1* | 8/2017 | Huang ............... G02B 21/0032 |
| 2017/0330327 A1* | 11/2017 | Ippolito ............... G02B 21/367 |

FOREIGN PATENT DOCUMENTS

| | | |
|---|---|---|
| JP | 2014-130221 A | 7/2014 |
| WO | 2014/208077 A1 | 12/2014 |

OTHER PUBLICATIONS

Feb. 7, 2017 International Search Report issued in International Patent Application No. PCT/JP2016/084865.

Mar. 19, 2020 Extended European Search Report issued in European Patent Application No. 16922471.4.

Lenz et al. "Display of Density Volumes." IEEE Computer Graphics and Applications, IEEE Service Center, New York, NY, US, vol. 4, No. 7, Jul. 1, 1986, pp. 20-29.

Sep. 24, 2021 Office Action issued in European Patent Application No. 16922471.4.

* cited by examiner

IMAGE PROCESSING DEVICE, MICROSCOPE SYSTEM, IMAGE PROCESSING METHOD, AND COMPUTER PROGRAM FOR DISPLAYING MAGNIFIED IMAGES FROM DIFFERENT OBSERVATION DIRECTIONS

CROSS-REFERENCE

This application is a U.S. national phase entry of International Application No. PCT/JP2016/084865 which was filed on Nov. 24, 2016, and the disclosure of international application no. PCT/JP2016/084865 is incorporated herein by reference in their entirety.

TECHNICAL FIELD

The present disclosure relates to an image processor, a microscope system, an image processing method, and a computer program.

BACKGROUND ART

There is a microscope that can generate a three dimensional microscope image including three dimensional position information regarding a specimen (see, for example, JP2010-243597A). An observation of the three dimensional microscope image was a difficult task requiring time.

SUMMARY

According to a first aspect of the present disclosure, an image processor including an accepting unit which accepts designation of at least a part of three dimensional microscope image data, and an image generator which generates three dimensional magnified image data based on the designation, is provided.

According to a second aspect of the present disclosure, a microscope system including the image processor, a microscope configured to output the microscope image data to the image processor, and a display configured to display an image output from the image processor, is provided.

According to a third aspect of the present disclosure, an image processing method including accepting designation of at least a part of the three dimensional microscope image data, and generating the three dimensional magnified image data based on the designation, is provided.

According to a fourth aspect of the present disclosure, a computer program configured to cause a computer to execute accepting designation of at least a part of the three dimensional microscope image data, and generating the three dimensional magnified image data based on the designation, is provided.

The aforementioned summary of the disclosure does not enumerate all the features of the present disclosure. The scope of the present disclosure may also include a subcombination of these feature groups.

DESCRIPTION OF EMBODIMENTS

Hereinafter, the present disclosure will be described through embodiments of the disclosure. The following embodiments do not limit the disclosure according to the claims. In addition, not all combinations of the features described in the embodiments are necessarily essential to the solutions of the disclosure.

Figure 1:
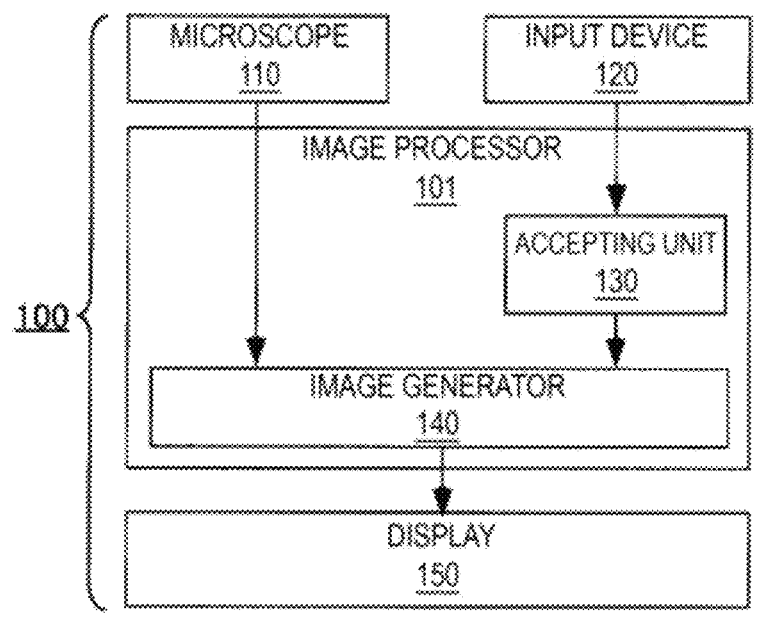
FIG. 1 is a block diagram of a microscope system 100.

FIG. 1 is a block diagram of a microscope system 100. The microscope system 100 includes an image processor 101, a microscope 110, an input device 120, and a display 150.

The microscope 110 is a confocal microscope. The confocal microscope generates image data for each of different focal planes in one specimen. The image data generated by the microscope 110 are output to the image processor 101.

The input device 120 outputs an instruction to the image processor 101 corresponding to an operation of a user. As the input device 120, a mouse and a keyboard can be used. Note that, as the input device 120, a joystick, a touch pad, a touch panel and the like may be used instead of the mouse. In addition to the mouse and the keyboard, a 3D mouse, a motion sensor and the like may be used together. The display 150 includes a liquid crystal display panel, and displays the image of the microscope output by the image processor 101 in a state in which the user can visually recognize.

The image processor 101 includes an accepting unit 130 and an image generator 140. The accepting unit 130 accepts an instruction from the input device 120 operated by the user, and reflects it on the image generator 140. In addition, the accepting unit 130 accepts starting, interruption, termination and the like of a processing, and reflects them on the operation of the image generator 140. In addition, in a case where the image generator 140 executes an image processing, the accepting unit 130 designates the type of the processing, accepts the options of the processing contents, the degree of the processing and the like from the user through the input device 120 and reflects them on the operation of the image generator 140.

The image generator 140 executes the image processing on the image data acquired from the microscope 110 according to the instruction accepted through the accepting unit 130. In addition, the image generator 140 generates an image according to the instruction accepted through the accepting unit 130, and outputs the image to the display 150.

As an example, the image generator 140 composes a plurality of image data (information of two-dimensional images of the specimen) regarding the different focal planes acquired from the microscope 110 and generates three dimensional microscope image data including information of a three dimensional intensity distribution (information of three dimensional images of the specimen). In addition, the image generator 140 generates a two-dimensional microscope image (two-dimensional microscope image data) based on the generated three dimensional microscope image data and outputs the image to the display 150 for displaying.

The image data from the microscope 110 is generated in a general-purpose format such as JPEG, BMP and the like. Note that, instead of this, the image data may be generated in a dedicated format capable of image processing by the image processor 101.

Note that, the two-dimensional microscope image generated from the three dimensional microscope image data by the image generator 140 can be paraphrased as a microscope image based on a part of the three dimensional microscope image data generated by the image generator 140 based on the image data acquired from the microscope 110. Furthermore, this two-dimensional microscope image can be paraphrased as an image generated by so-called rendering of the three dimensional microscope image data.

Figure 2:
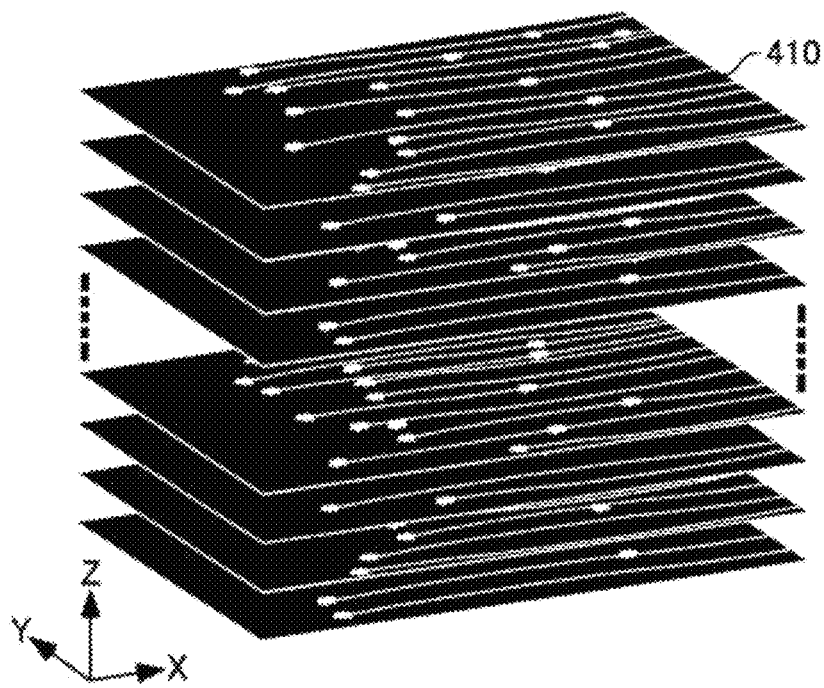
FIG. 2 is a schematic view of an image data 410 output by a microscope.
Figure 3:
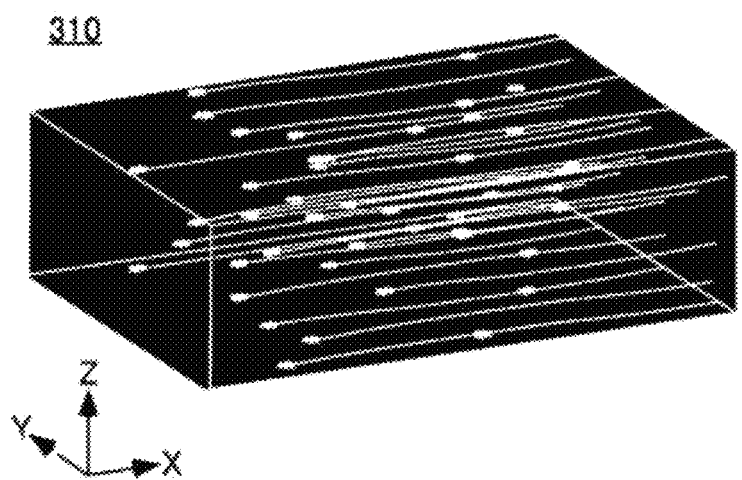
FIG. 3 is a schematic view of a three dimensional microscope image data 310.

FIG. 2 and FIG. 3 are schematic views illustrating a processing in which the image generator 140 generates the three dimensional microscope image data 310 from a plurality of image data 410 acquired by the microscope 110. In FIG. 2 and FIG. 3, an orthogonal coordinate system (X-Y-Z coordinate system) is described for description. The image data 410 is data of an image illustrating the distribution of fluorescence intensity in the specimen generated by capturing at one focal plane of the specimen by the microscope 110. The microscope 110 acquires the image data 410 on each of a plurality of different focal planes.

In a case where each of the focal planes of the image data 410 is a plane parallel to the X-Y plane in the coordinate system in the diagram, the image generator 140 generates the three dimensional microscope image data 310 illustrated in FIG. 3 by stacking the image data 410 in the Z axis direction and reconstructing the intensity distribution between each focal plane. In other words, the image generator 140 generates the three dimensional microscope image data 310 by stacking and composing a plurality of two-dimensional image data including pixels arranged in two dimensions. Here, the pixel is a minimum unit when handling the two-dimensional image data as an image, and each pixel includes an intensity value. The three dimensional microscope image data 310 includes information of three dimensional intensity distribution.

The three dimensional microscope image data 310 can be paraphrased as a three dimensional image data having a structure in which a plurality of layers of a plurality of pixels arranged in two-dimensions are stacked. In addition, the aforementioned three dimensional microscope image data also can be paraphrased as three dimensional image data formed by voxels arranged in three-dimensions. Note that, in the following description, the pixels and the voxels of the aforementioned three dimensional microscope image data 310 are also collectively referred to as "pixels". In addition, the orthogonal coordinate system (X-Y-Z coordinate system) illustrated in the diagram is described to indicate the orientation of the three dimensional microscope image data 310.

In addition, the three dimensional microscope image data 310 are handled as image data (for example, processed as image data in the image processor 101) until the data are displayed on the display 170. Therefore, hereinafter, the data are referred to as the three dimensional microscope image data 310. Further, since the information indicated by the data is an image, it is appropriately referred to as the three dimensional microscope image 310 using the same reference numerals for convenience of description. The three dimensional magnified image data 340 to be described hereinafter is also referred to as a three dimensional magnified image 340 by using the same reference numerals for convenience of description.

Further, as described above, as the microscope 110 capable of acquiring the intensity distribution at different focal planes, STochastic Optical Reconstruction Microscopy (STORM), Structured Illumination Microscopy (SIM), Light Sheet Fluorescence Microscopy (LSFM), STimulated Emission Depletion (STED), PhotoActivated Localization Microscopy (PALM), phase-contrast microscope, differential interference microscope, electron microscope and the like, existing microscope can be exemplified. In addition, images obtained by other than the existing microscope, for example, an image acquired by Magnetic Resonance Imaging (MRI), Computed Tomography (CT), Positron Emission Tomography (PET) and the like may be used.

Figure 4:
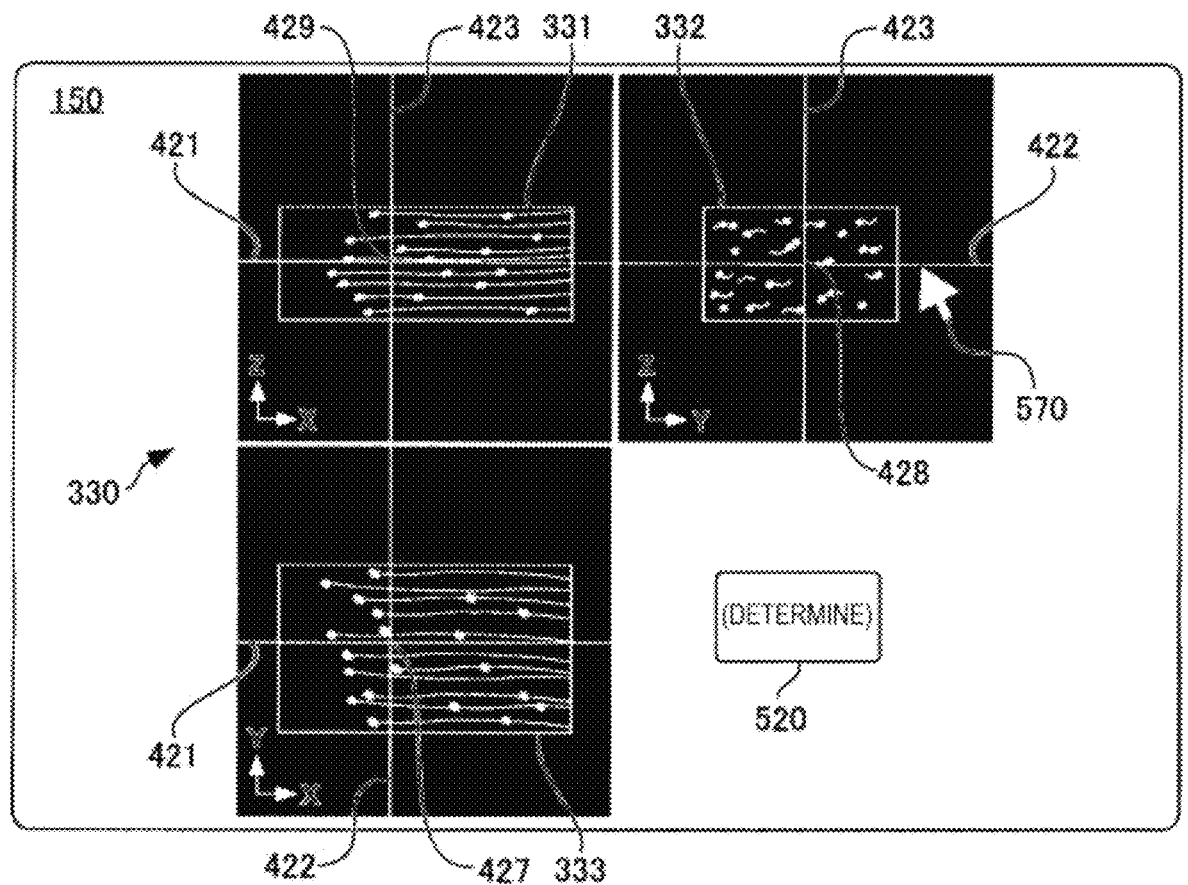
FIG. 4 is a diagram illustrating an image displayed on a display 150.

As illustrated in FIG. 4, the image generator 140 causes the display 150 to display microscope images 331, 332, 333 generated based on the three dimensional microscope image data as described above, and the accepting unit 130 accepts designation of at least a part of the three dimensional microscope image data 310 by accepting designation of the positions of the microscope image 331, 332, 333.

In the example of FIG. 4, the display 150 displays a three-sided view 330 including three microscope images 331, 332, 333 and a button 520. The microscope image 331 is an image of the lateral face parallel to the X-Z plane of the three dimensional microscope image 310 illustrated in FIG. 3, the microscope image 332 is an image of the lateral face parallel to the Y-Z plane, the microscope image 333 is an image of the lateral face parallel to the X-Y plane.

It can be said that the microscope images 331, 332, 333 are parts of the three dimensional microscope image data 310. Furthermore, the microscope images 331, 332, 333 can be paraphrased as an image generated by so-called rendering of the three dimensional microscope image data 310.

In the microscope image 331, a straight line 421 parallel to the X axis and a straight line 423 parallel to the Z axis in the three dimensional orthogonal coordinate system are displayed in an overlapping manner. The straight lines 421 and 423 are orthogonal to each other. The straight lines 421 and 423 can be individually moved by overlapping a mouse cursor 570 and dragging the mouse. The accepting unit 130 accepts a movement in a direction orthogonal to the extending direction of the straight lines 421 and 423. As a result, the accepting unit 130 accepts designation of a position of the intersection 429 of the straight lines 421, 423 in the microscope image 331 by the operating of the mouse serving as the input device 120 from the user.

Similarly, in the microscope image 332, a straight line 422 parallel to the Y axis and a straight line 423 parallel to the Z axis in the aforementioned three dimensional orthogonal coordinate system are displayed in an overlapping manner. The straight lines 422 and 423 are orthogonal to each other and can be moved individually by dragging the mouse. The accepting unit 130 accepts a movement in a direction orthogonal to the extending direction of the straight lines 422 and 423. As a result, the accepting unit 130 accepts designation of a position of the intersection 428 of the straight lines 422, 423 in the microscope image 332 by the operating of the mouse serving as the input device 120 from the user.

Further, in the microscope image 333, a straight line 421 parallel to the X axis and a straight line 422 parallel to the Y axis in the aforementioned three dimensional orthogonal coordinate system are displayed in an overlapping manner. The straight lines 421 and 422 are orthogonal to each other and can be moved individually by dragging the mouse. The accepting unit 130 accepts a movement in a direction orthogonal to the extending direction of the straight lines 421 and 422. As a result, the accepting unit 130 accepts designation of a position of the intersection 427 of the straight lines 421, 422 in the microscope image 333 by the operating of the mouse serving as the input device 120 from the user.

Since the microscope images 331, 332, 333 are images based on the same three dimensional microscope image data 310, in a case where either one of the aforementioned straight line 421 overlapping with the microscope image 331 and the straight line 421 overlapping with the microscope image 333 is moved, the other is also interlocked. In addition, in a case where either one of the straight line 422 overlapping with the microscope image 332 and the straight line 422 overlapping with the microscope image 333 is moved, the other is also interlocked. Further, in a case where either one of the straight line 423 overlapping with the microscope image 333 and the straight line 422 overlapping with the microscope image 331 is moved, the other is also interlocked.

Therefore, it is possible to designate a position of one point in the three dimensional microscope image data 310 when the three straight lines 421, 422, 423 are moved in any two of the three microscope images 331, 332, 333. The microscope images 331, 332, 333 can be paraphrased as an image for position designation.

Further, in a case where the user operates the mouse as the input device 120 to press the button 520 displayed together with the three-sided view 330 on the display 150, the accepting unit 130 accepts the position designated by the intersections 427, 428, 429 of the straight lines 421, 422, 423 as the designated position.

Figure 6:
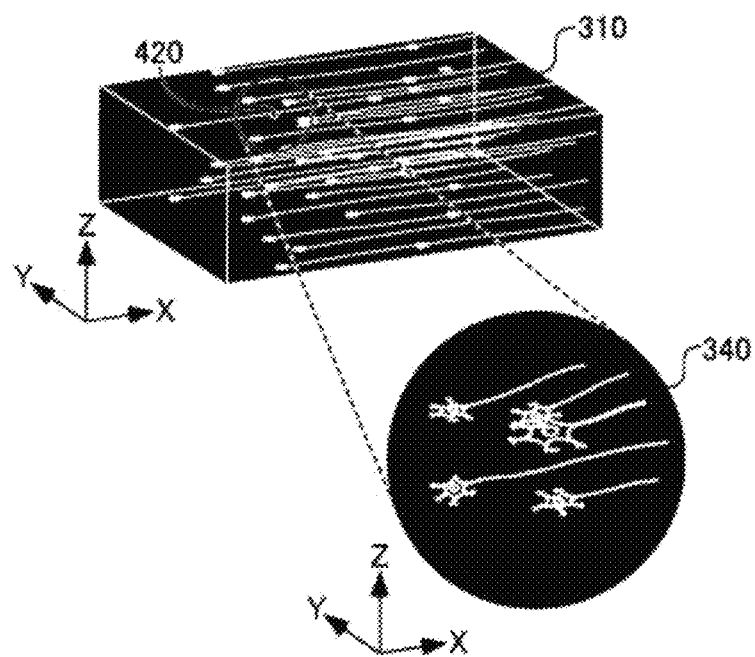
FIG. 6 is a schematic view describing a concept of the three dimensional magnified image data 340.

As illustrated in FIG. 6, the image generator 140 identifies a part 350 (that is, a part of the three dimensional microscope image 310) of the three dimensional microscope image data 310 to be magnified, based on the designated position 420 accepted by the accepting unit 130. In the example illustrated in FIG. 6, the image generator 140 identifies a sphere having a predetermined radius centering at the designated position 420 as the part 350. Note that, the part 350 of the three dimensional microscope image data 310 identified based on the designated position 420 may be in other shapes, such as a cone, a polygonal pyramid, a cylinder, a polygonal prism, a polyhedron and the like. The shape of the part 350 is set by default, so that the user can select the shape of the part 350 by the input device 120.

The image generator 140 generates the three dimensional magnified image data 340 that magnifies the part 350 of the three dimensional microscope image 310 identified based on the designated position 420. In the example illustrated in FIG. 6, the image generator 140 generates the three dimensional magnified image data 340 representing a spherical three dimensional image, corresponding to the part 350 being spherical.

The three dimensional magnified image data 340 can also be said to be data of an image displayed larger than the part 350 of the three dimensional microscope image 310 on the display 150. Note that, in the generated three dimensional magnified image data 340, in a case where a part of pixels forming an image is insufficient and a missing occurs in the image, the image generator 140 may generate pixels for complementation to compensate the missing pixels.

Figure 5:
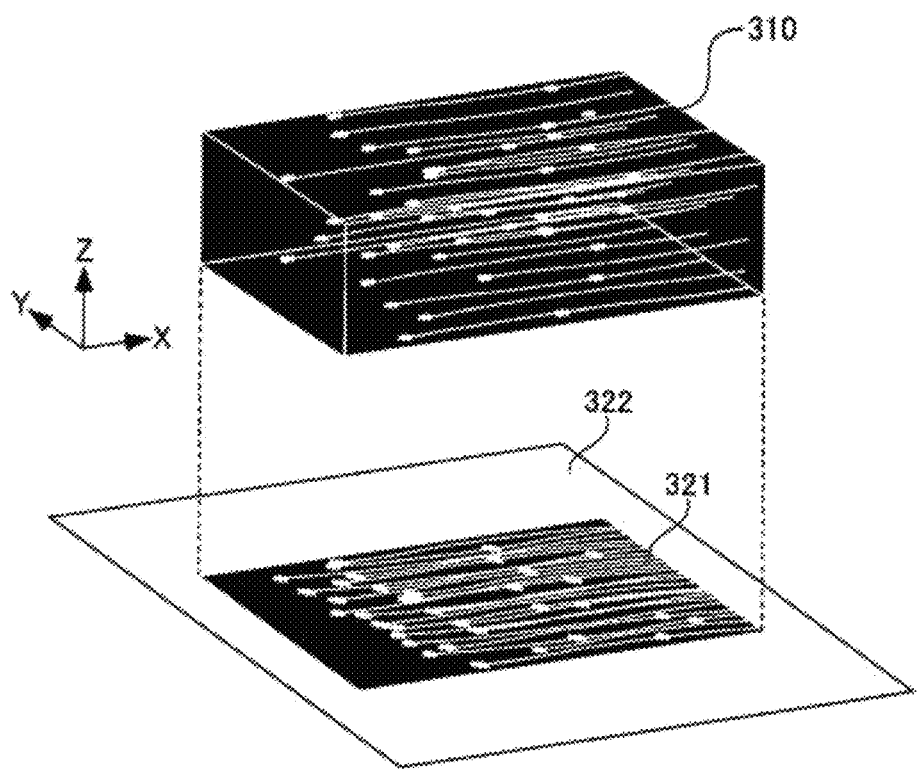
FIG. 5 is a diagram illustrating an image displayed on the display 150.

The image generator 140 generates a display microscope image 321 illustrated in FIG. 5 from the three dimensional microscope image data 310. In addition, the image generator 140 generates the magnified image 341 illustrated in FIG. 7 from the three dimensional magnified image data 340.

In the example illustrated in FIG. 5, the image generator 140 generates the two-dimensional display microscope image 321 by projecting an image (three dimensional microscope image 340) based on the three dimensional microscope image data 310 onto a projection plane 322. Here, it can be paraphrased that the display microscope image 321 is a part of the three dimensional microscope image data 310. Furthermore, the display microscope image 321 can be paraphrased as an image generated by so-called rendering of the three dimensional microscope image data 310.

Figure 7:
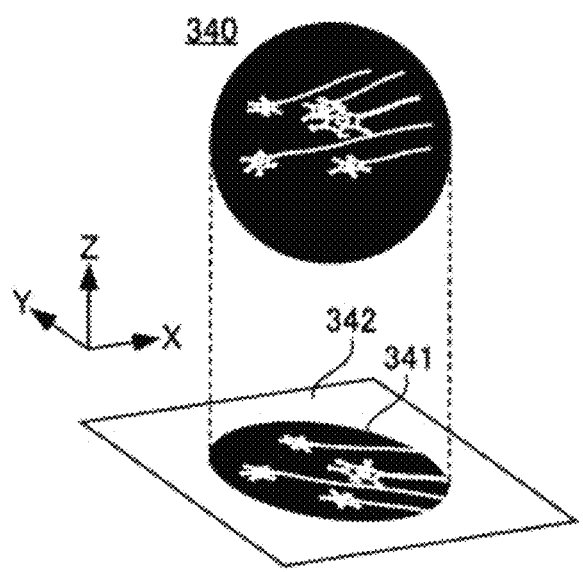
FIG. 7 is a schematic view of a magnified image 341.

In the example illustrated in FIG. 7, the image generator 140 projects an image (three dimensional magnified image 340) based on the three dimensional magnified image data 340 onto a projection plane 342 to generate the magnified image 341. Since the three dimensional magnified image data 340 is data of an image which magnified a part 250 including the designated position 420 in the three dimensional microscope image 310, the magnified image 341 is an image magnified to be larger than the display microscope image 321. Therefore, in the microscope system 100, in a case where the designated position 420 from the user in the three dimensional microscope image 310 is accepted, the magnified image 341 based on the three dimensional magnified image 340 which magnified a region including the designated position 420 is displayed, thus the three dimensional microscope images can be observed in detail. As a result, the observation of the three dimensional microscope images becomes easy.

In addition, the magnified image 341 generated by the image generator 140 from the three dimensional magnified image data 340 can also be paraphrased as being a part of the three dimensional microscope image data 310 generated by the image generator 140. Furthermore, the magnified image 341 can also be paraphrased as being an image generated by so-called rendering of the three dimensional magnified image data 340.

Further, in a case where the three dimensional magnified image 340 is projected onto the projection plane 342, the image generator 140 may generate the magnified image 341 by projecting an image having an intensity higher than a predetermined threshold. As a result, with the contrast of the magnified image 341 is increased, the magnified image 341 represented by the information on the internal structure of the specimen included in the three dimensional magnified image data 340 can be generated. As a result, it becomes easier to observe the point to be noted, and the observation of the three dimensional microscope images becomes easy in the magnified image 341.

Figure 8:
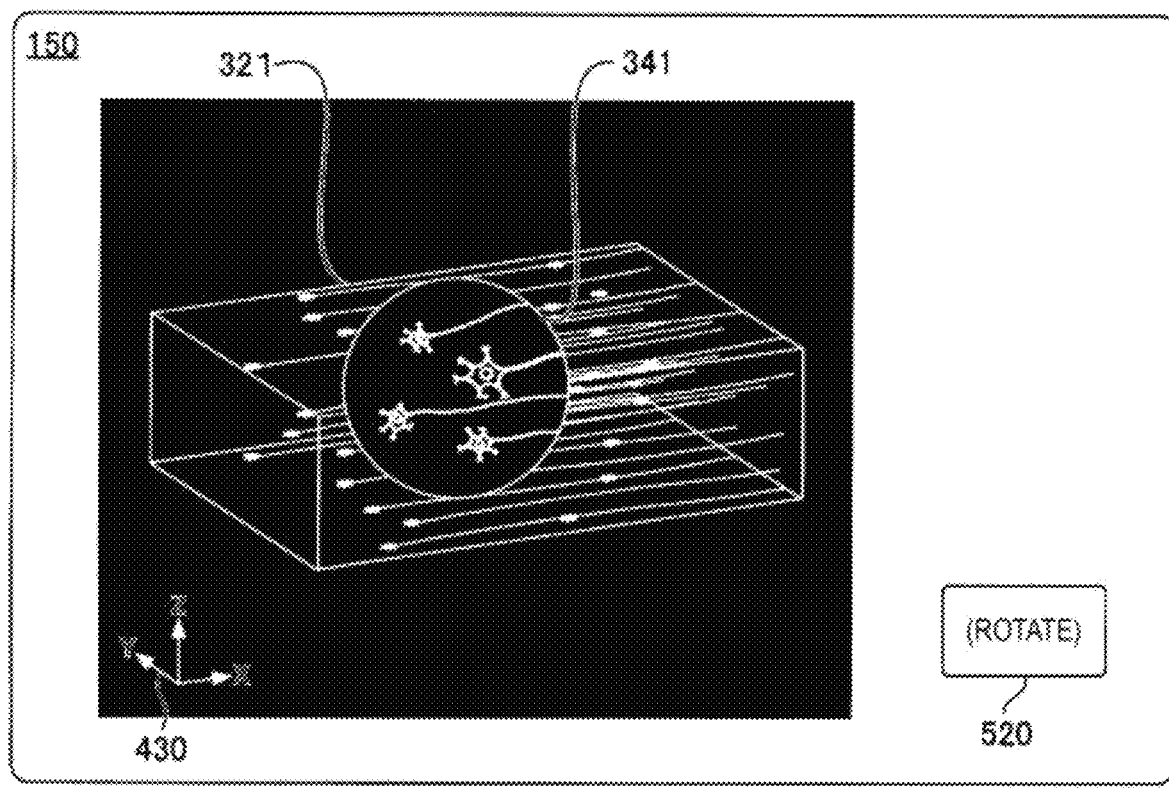
FIG. 8 is a diagram illustrating an image displayed on the display 150.

FIG. 8 is a diagram illustrating an image caused to display on the display 150 by the image generator 140 after generating the magnified image 341. The image generator 140 generates an image in which the generated magnified image 341 is overlapped on the display microscope image 321, and displays the generated image on the display 150.

Here, the magnified image 341 is superimposed on the display microscope image 321 such that the position of the center of the magnified image 341 coincides with the designated position designated by the user. As a result, the position of the magnified image 341 in the entire display microscope image 321 is intuitively understood, thus observation of the three dimensional microscope images by the microscope becomes easier.

In addition, in the microscope system 100, since a part of the three dimensional microscope image 310 is magnified and displayed on the display 150, load on the image processing related to the generation of the magnified images is small and a smooth image displaying is enabled. Therefore, the observation of the three dimensional microscope image 310 becomes easy.

Figure 9:
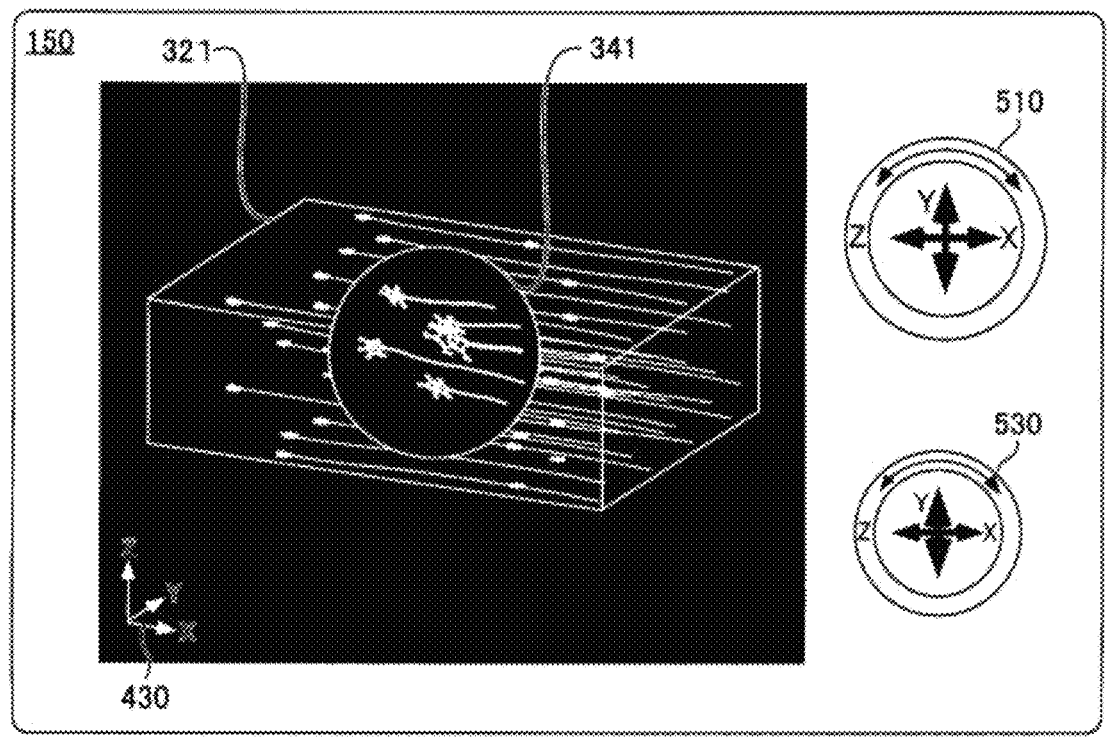
FIG. 9 is a diagram illustrating an image displayed on the display 150.

FIG. 9 is a diagram configured to describe another image processing by the image generator 140. In a case where the mouse cursor was placed on the button 520 displayed on the screen of the display 150 and the mouse button was pressed down in FIG. 8, as illustrated in FIG. 9, two keys 510 and 530 are displayed on the display 150 together with the display microscope image 321 on which the magnified image 341 is superimposed.

Further, in a case where an operation of overlapping the mouse cursor on the key 510 displayed on the upper side in the diagram and pressing down the mouse button is accepted, the display microscope image 321 changes as if the three dimensional microscope image 310 rotated in the rotation direction by the rotation amount identified by a position of the mouse cursor on the key 510. In the example of FIG. 9, the display microscope image 321 is displayed such that the three dimensional microscope image 310 rotated around the Z axis from the state of FIG. 8. This can be said that, virtually, the image generator 140 causes the tilt of the three dimensional microscope image 310 with respect to the projection plane 322 illustrated in FIG. 5 to change, and generates and displays a new display microscope image 321 obtained by projecting the three dimensional microscope image 310 onto the projection plane 322.

Similarly, the magnified image 341 changes as if the three dimensional magnified image 340 was rotated in the rotation direction by the rotation amount identified by the position of the mouse cursor on the key 510. In the example of FIG. 9, the magnified image 341 is displayed such that the three dimensional magnified image 340 rotated around the Z axis from the state of FIG. 8. Virtually, the image generator 140 changes the tilt of the three dimensional magnified image 340 with respect to the projection plane 322 illustrated in FIG. 7, generates a new magnified image 341 obtained by projecting the three dimensional magnified image 340 onto the projection plane 322, and displays the magnified image 341. Note that, the projection plane 322 is a virtual plane for description. The image generator 140 superimposes the newly generated magnified image 341 on the newly generated display microscope image 321 and outputs it to the display 150. In this way, the state in which the three dimensional microscope image 310 and the three dimensional magnified image 340 rotate in synchronization is displayed on the display 150 by sequentially displaying the new display microscope image 321 and the magnified image 341 each time the key 510 is operated. As a result, it is possible to comprehensively observe the three dimensional microscope image 310 from various directions. Therefore, the observation of the three dimensional microscope image 310 becomes easy.

Here, the image generator 140 superimposes the magnified image 341 on the display microscope image 321 such that the positional relationship in which the designated position 420 designated by the user in the three dimensional microscope image 310 coincides with the center of the magnified image 341 is continued to maintain. As a result, the user can more easily grasp the positional relationship between the magnified image 341 and the display microscope image 321 even if the observation direction is changed, and the observation of the three dimensional microscope image 310 becomes easier.

Figure 10:
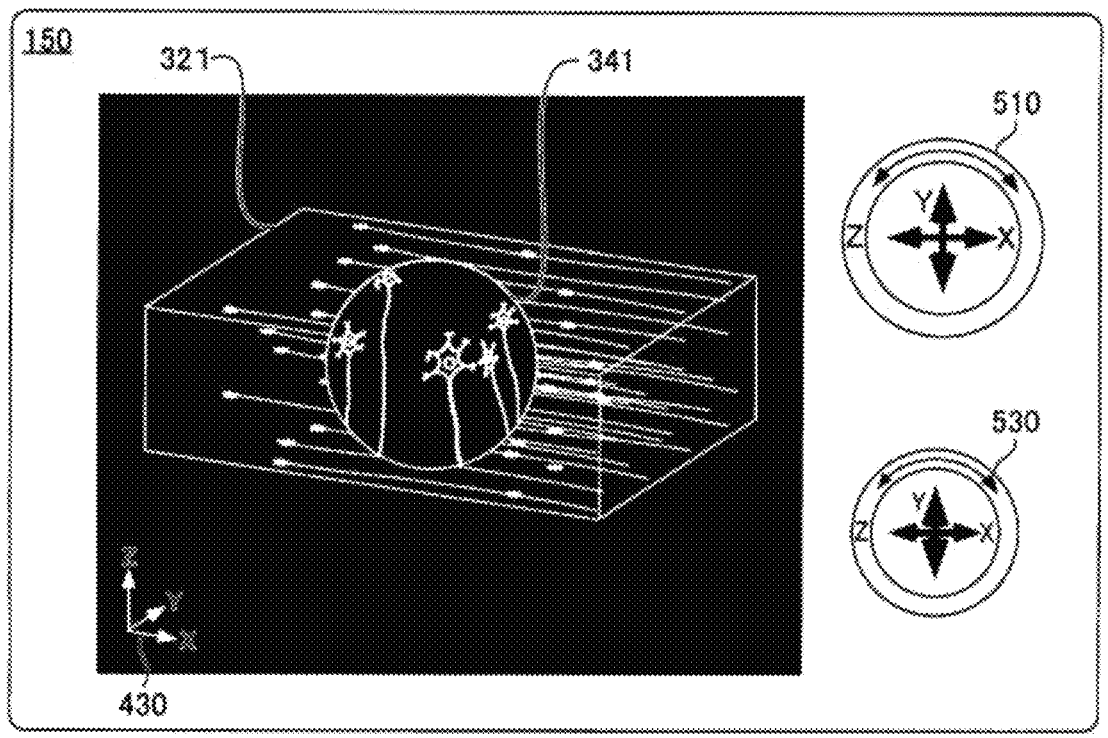
FIG. 10 is a diagram illustrating an image displayed on the display 150.

FIG. 10 is a diagram configured to describe a processing executed by the image generator 140 in a case where the key 530 positioned on the lower side in the diagram is operated, in a state in which the image illustrated in FIG. 9 is displayed on the display 150. The operation method of the key 530 is the same as that of the key 510. In a case where the accepting unit 130 accepts input of operation of the key 530 via the mouse, the image generator 140 displays the magnified image 341 in which the observation direction is changed only for the three dimensional magnified image 340.

As a result, the magnified image 341 corresponding to the change in the observation direction is sequentially displayed in a state in which the display microscope image 321 is fixed. Therefore, it is possible to comprehensively observe the region to be focused from various directions. In addition, it is possible to observe the three dimensional magnified image in detail by the magnified image 341 without increasing the processing load on the image processor 101. Therefore, observation of the three dimensional images by microscope becomes easier.

Note that, in the aforementioned example, the accepting unit 130 accepted input of rotation via the keys 510 and 530 displayed on the display 150 together with the display microscope image 321 and the magnified image 341. However, keys 510 and 530 may not be used. For example, in a case where the mouse is operated by dragging in a state in which the mouse cursor is positioned within the region where the display microscope image 321 and the magnified image 341 are displayed on the display 150, the input of rotation according to the drag operation may be accepted. For example, in a case where the accepting unit 130 accepted an operation of dragging (in the −Z direction) and pulling down the position above (+Z direction) the display microscope image 321, the image generator 140 generates a new display microscope image 321 corresponding to the case where the three dimensional microscope image 310 is rotated about the Z axis. Similarly, the image generator 140 generates a new magnified image 341 corresponding to the case where the three dimensional magnified image 340 is virtually rotated about the X axis orthogonal to the Z axis. As a result, by more intuitively operating the input of the three dimensional microscope image 310 and three dimensional magnified image 340 in the observation direction, the observation of the three dimensional images by the microscope can become easier.

Figure 11:
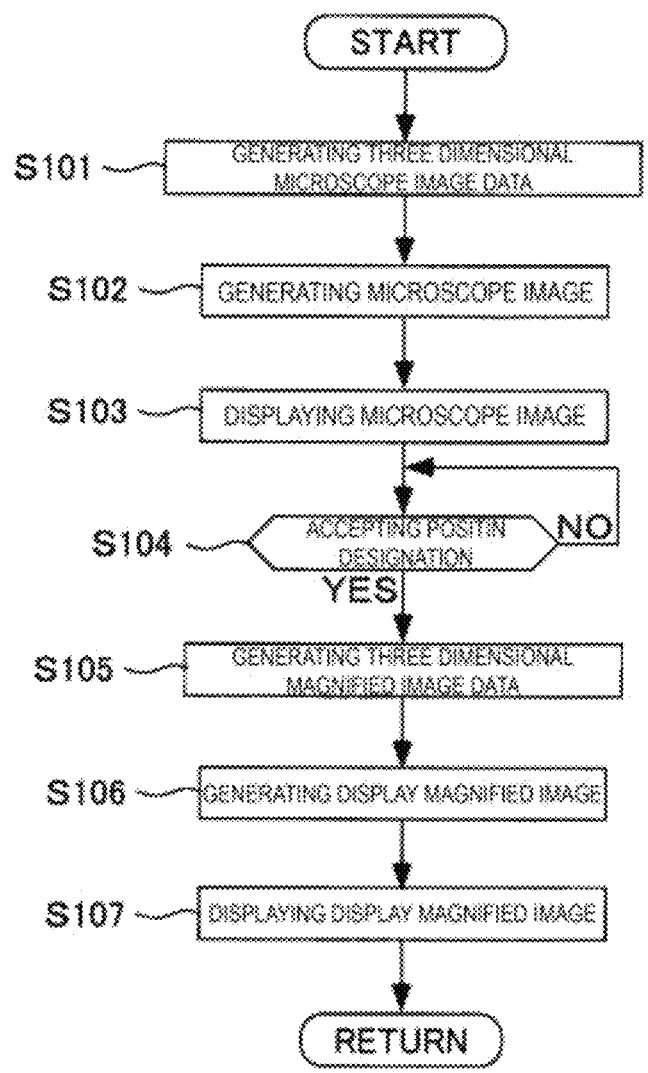
FIG. 11 is a flowchart of a processing executed by an image processor 101.

FIG. 11 is a flowchart illustrating a processing procedure of the image processor 101. When an image processing by the image processor 101 is started, first, the image generator 140 generates the three dimensional microscope image data 310 as illustrated in FIG. 2 and FIG. 3 based on a plurality of the image data 410 acquired from the microscope 110. (Step S101).

Next, the image generator 140 generates the three-sided view 330 for position designation including a plurality of microscope images 331, 332, 333 (step S102) based on the three dimensional microscope image data 310, and displays the three-sided view 330 on the display 150 as illustrated in FIG. 4 (step S103). Next, the image generator 140 waits for the accepting unit 130 to accept the designated position designated by the user with respect to the displayed three-sided view 330 (step S104: NO).

Next, in step S104, when the designated position is determined by the user (step S104: YES), the image generator 140 identifies a region including the designated position in the three dimensional microscope image 310 and generates the three dimensional magnified image data 340 in which the region is magnified (step S105). Further, the image generator 140 generates the magnified image 341 to be displayed on the display 150 based on the three dimensional magnified image data 340 (step S106).

Next, the image generator 140 causes the display 150 to display the generated magnified image 341 (step S107), and terminates the processing. Thus, the user can observe the magnified image of the region including the designated position 420 designated via the three-sided view 330. In this way, the microscope system 100 including the image processor 101 can easily input designation of a region to be focused on. In addition, since only the designated position or the region is processed in the three dimensional microscope image data 310, the processing load is light and operates smoothly. Therefore, the efficiency of the observation of the three dimensional microscope images by the microscope is improved, and necessary labor and time are reduced, such that the observation becomes easy.

Note that, in the aforementioned embodiment, in a case where the position is designated, the microscope images 331, 332, 333 of three planes of the three dimensional microscope image data 310 are used. However, since one point in the three dimensional microscope image data 310 can be designated by microscope images of two planes intersecting with each other in the three dimensional microscope image data 310, only microscope images of two planes may be displayed. In addition, the microscope images of four or more planes may be displayed. In a case of displaying the microscope images of four or more planes, a microscope image viewed from a direction tilt with respect to any of the three dimensional microscope image data 310 may be included.

In addition, the size of display of some microscope images may be different in a case where displaying a plurality of microscope images. For example, in order to designate the position, the microscope image in the middle while moving the straight lines 421, 422, 423 may be displayed larger, and the other microscope images may be displayed smaller.

Note that, in the aforementioned embodiment, the two-dimensional microscope image for position designation generated from the three dimensional microscope image data 310 by the image generator 140 is the microscope images 331, 332, 333 on the three lateral faces of the three dimensional microscope image data 310, but the image also may be an image of an arbitrary cross section of the three dimensional microscope image 310. Further, the two-dimensional microscope image for position designation generated from the three dimensional microscope image data 310 by the image generator 140 may be an image generated by projecting the three dimensional microscope image 310 onto an arbitrary plane. In this case, the image generator 140 may use the three two-dimensional microscope images obtained by projecting the three dimensional microscope image 310 onto three virtual projection planes intersecting each other instead of the aforementioned microscope images 331, 332, 333 on the three lateral faces. Further, the microscope image for position designation may be generated by another existing method configured to generate a two-dimensional image from the three dimensional image data.

Figure 12:
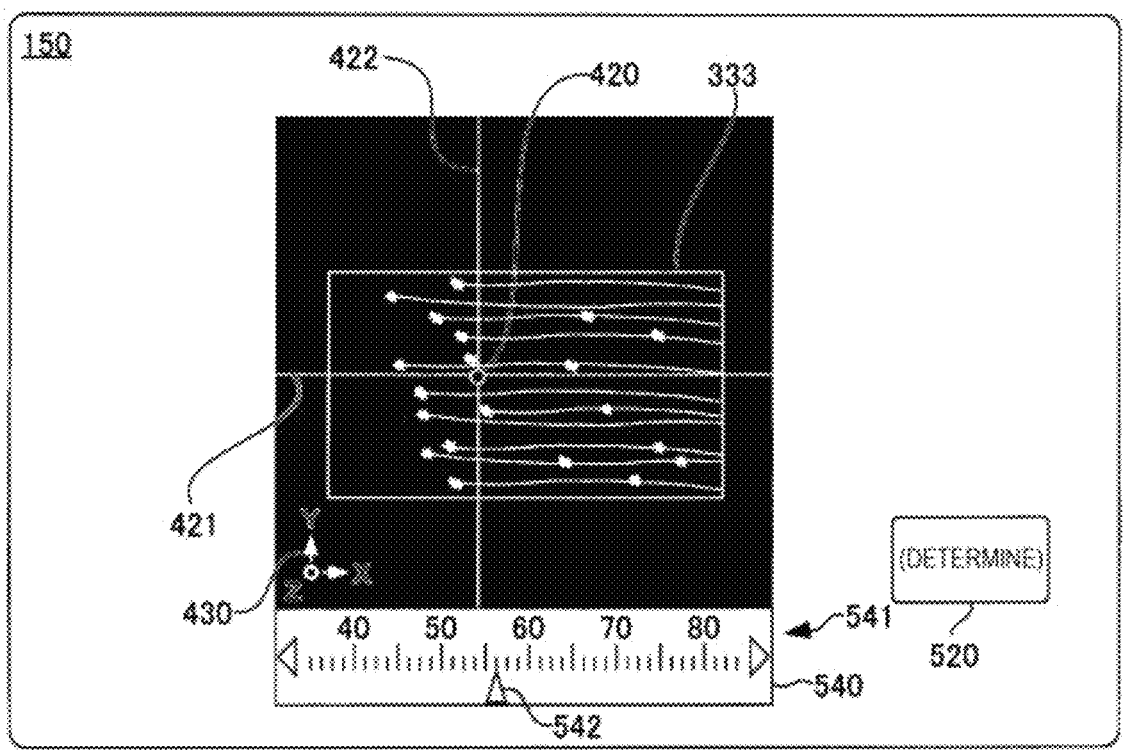
FIG. 12 is a diagram illustrating an image displayed on the display 150.

FIG. 12 is a diagram configured to describe a modification of an operation of designating a designated position in the image processor 101 via the input device 120. FIG. 12 illustrates an image displayed on the display 150.

In the example illustrated in FIG. 12, in step 103 of FIG. 11, the image generator 140 displays the microscope image 333 on the display 150 as an image for position designation in which data (that is, the position of a part of the three dimensional microscope image 310) of part of the three dimensional microscope image data 310 is designated. In addition, the image generator 140 displays a slider 540 disposed below the microscope image 323 together with the button 520 arranged at a position distant from the microscope image 323 on the display 150.

The image generator 140 generates the microscope image 333 which is an image of a cross section obtained by cutting the three dimensional microscope image 310 (three dimensional microscope image data 310) along a plane perpendicular to the Z axis and displays it on the display 150 for position designation.

The slider 540 to be displayed by the image generator 140 includes a scale 541 and a knob 542. The knob 542 indicates the number of the microscope images 333 currently displayed on the display 150 among the plurality of the microscope images 333 aligned in the Z axis direction by the opposing scale 541. In addition, the number of the microscope image 333 to be displayed on the display 150 among the plurality of the microscope images 333 aligned in the Z axis direction can be selected by sliding the knob 542 horizontally in the diagram by mouse dragging. Thus, the image generator 140 displays the designated microscope image 333 on the display 150 by the user sliding the knob 542 with the mouse. Note that, instead of the scale 541 of the slider 540, an indicator indicating the position in the Z axis direction of the microscope image 333 such as the Z coordinate in the three dimensional microscope image 310 may be illustrated on the horizontal axis of the slider 540.

Further, also in the example illustrated in FIG. 12, as in FIG. 4, the straight line 421 parallel to the X axis of the orthogonal coordinate system indicated by a marker 430 and the straight line 422 similarly parallel to the Y axis are displayed in an overlapping manner on the microscope image 333. The straight lines 421 and 423 can be individually moved by overlapping the cursor 570 and dragging the mouse. In the case of moving the straight lines 421 and 422, the straight lines 421 and 422 move in a direction perpendicular to their respective extending directions. Therefore, it is possible to move the straight lines 421 and 422, and move the intersection 429 of the straight lines 421 and 423 to one point in the display microscope image 331 by operating the mouse as the input device 120.

Thus, it is possible to designate the position in the Z direction in the three dimensional coordinate indicated by the marker 430, and furthermore, it is possible to move the straight lines 421 and 422, and move the intersection of the straight line 421, 422 to one point in the microscope image 333 by operating the mouse as the knob 542 of the slider 540.

Further, in step S104 of the FIG. 11, when the user operates the mouse as the input device 120 and presses the button 520 displayed on the display 150, the accepting unit 130 accepts the position where the straight lines 421 and 422 is intersected on the plane formed by the selected microscope image 333 as the designated position 420. Here, the position in the Z direction is designated by the selection of the identified microscope image 333 and the position in the XY plane is designated by the position designation in the microscope image 333. Therefore, it can be said that the designated position 420 designates the position in the three dimensional space.

Further, the image generator 140 identifies a region including the designated position 420 in the three dimensional microscope image 310, and generates the three dimensional magnified image data 340 in which the region is magnified (step S105 in FIG. 11). Further, the image generator 140 generates the magnified image 341 to be displayed on the display 150 (step S106 in FIG. 11), and displays the magnified image 341 on the display 150 (step S107) based on the three dimensional magnified image data 340.

In this way, in the example illustrated in FIG. 12, it is possible to easily designate the position (a part of data in the three dimensional microscope image data 310) in the three dimensional microscope image 310 by combining any one of the identification from the plurality of the microscope images 333 aligned in the Z axis direction and the designated position in the plane of the identified microscope image 333. As a result, the magnified image 341 obtained by magnifying the region including the position is displayed in steps S105 to S106, thus observation of the three dimensional microscope images can become easy.

In addition, in the aforementioned example, the image generator 140 displays a microscope image obtained by cutting the three dimensional microscope image data 410 at a cross section parallel to the X-Y plane and selects the microscope image. However, the plane formed by the microscope image to be displayed by the image generator 140 is not limited to a plane parallel to the X-Y plane, but may be a plane parallel to the Y-Z plane or the X-Z plane. In addition, it is also possible to use a microscope image formed on a plane which is not parallel to any coordinate axis.

Figure 13:
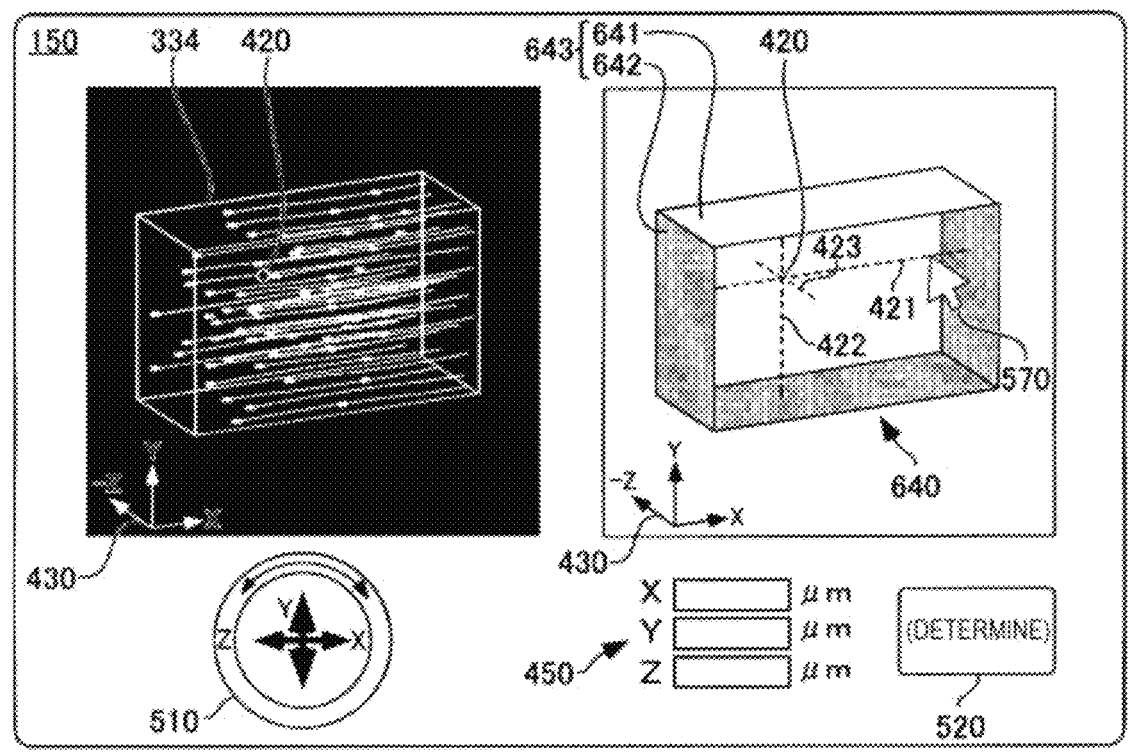
FIG. 13 is a diagram illustrating an image displayed on the display 150.

FIG. 13 is a diagram configured to describe another example of steps S102 to S104 in FIG. 11. FIG. 13 illustrates an image displayed on the display 150. In the example of FIG. 13, instead of generating and displaying a microscope image 334 for position designation in steps S102 and S103, a reference image 440 for position designation is generated and displayed.

In the example illustrated in FIG. 13, the image generator 140 displays the display microscope image 334 on the left side in the diagram and the reference image 440 on the right side in the diagram on the display 150. In addition, the image generator 140 displays the key 510 below the display microscope image 334, and a field 450 and the button 520 below the reference image 440, respectively.

The display microscope image 334 displayed by the image generator 140 in FIG. 13 is generated by the image generator 140 by projecting the three dimensional microscope image data 310 onto the projection plane 322. Here, the display microscope image 334 changes as if the three dimensional microscope image 310 rotated in the rotation direction by the rotation amount identified by the position of the mouse cursor on the key 510, by accepting the operation of the accepting unit 130 of pressing the key 510 with the mouse, similarly to the description in FIG. 9. In the example of FIG. 9, the display microscope image 321 is displayed such that the three dimensional microscope image 310 rotated around the Z axis from the state of FIG. 8. It can be said that, virtually, the image generator 140 causes the tilt of the three dimensional microscope image 310 with respect to the projection plane 322 illustrated in FIG. 5 to change, and generates and displays the new display microscope image 334 obtained by projecting the three dimensional microscope image 310 onto the projection plane 322. Note that, the projection plane 322 is a virtual plane for description.

The reference image 440 generated and displayed by the image generator 140 is generated by projecting the three dimensional reference image data which is generated based on the three dimensional microscope image data 310 onto the projection plane by the image generator 140. Here, for example, the three dimensional reference image data is data representing an image in which the information (intensity distribution) of the image in the three dimensional microscope image 310 is deleted, and the generation region (corresponding to the outer frame of the reference image 440) of the three dimensional microscope image 310 is left.

For example, as illustrated in FIG. 5, in a case where the generation region of the three dimensional microscope image 310 is a rectangular parallelepiped, the reference image 440 displayed on the display 150 forms a short tubular frame 443 by two pairs of wall surfaces 441 and 442 which are opposed to each other in parallel.

Further, in a case where the accepting unit 130 accepted an operation of pressing the key 510 with the mouse, the image generator 140 generates the new display microscope image 324 corresponding to the rotation amount and the rotation direction by the operation as described above, and the new reference image 440 corresponding to the same rotation amount and rotation direction is also generated and displayed. Therefore, on the screen of the display 150 illustrated in FIG. 13, the display microscope image 334 and the reference image 440 are always displayed in the same direction.

Note that, the three dimensional orthogonal coordinate system indicated by the marker 430 is always parallel to any two surfaces of the rectangular parallelepiped formed by the reference image 440. Therefore, in a case where the display microscope image 334 is updated by operating the key 510 with the mouse, the orientation of the marker 430 is also updated along with the update of the reference image 440.

In addition, the image generator 140 displays three straight lines 421, 422, 423 parallel to the X axis, the Y axis, or the Z axis of the three dimensional coordinate system indicated by the marker 430 in the diagram inside the reference image 440. Each of the straight lines 421, 422, 423 can be individually moved by dragging the mouse. Note that, each of the straight lines 421, 422, 423 moves only in a direction perpendicular to their extending directions.

In addition, the straight lines 421, 422, 423 are orthogonal to each other, and three lines intersect at one point. Therefore, for example, the straight line 423 also moves in the Y direction in a case where the straight line 421 is moved in the Y axis direction indicated by the marker 430, and the straight line 422 also moves in the Z direction in a case where the straight line 421 is moved in the Z direction. Therefore, the intersection of the straight lines 421, 422, 423 can be moved to an arbitrary position within the space formed by the three dimensional reference image data by moving two of the three straight lines 421, 422, 423.

In other words, in the microscope system 100, the designated position 420 can be determined by operating the input device 120 and moving two of the straight lines 421, 422, 423. Further, in the microscope system 100, by pressing the button 520 by a mouse click operation as the input device 120, the input designated position 420 can be determined.

Further, the image generator 140 identifies a region including the designated position 420 in the three dimensional microscope image 310, and generates the three dimensional magnified image data 340 in which the region is magnified (step S105 in FIG. 11). Further, the image generator 140 generates the magnified image 341 to be displayed on the display 150 (step S106 in FIG. 11), and displays the magnified image 341 on the display 150 (step S107) based on the three dimensional magnified image data 340.

According to the example of FIG. 13, the designated position in the three dimensional microscope image data 310 can be easily designated by operating the straight lines 421, 422, 423 in the briefly displayed reference image 440 with the mouse. As a result, observation of the three dimensional images by the microscope can become easy.

Note that, as described above, it is possible to designate an arbitrary position in the three dimensional microscope image data 310 by moving two of the three straight lines 421, 422, and 423. Therefore, it is also possible to simplify the display by setting two straight lines to be displayed in the reference image 440. As a result, the burden of the processing of the image generator 140 can be reduced.

In addition, in the example illustrated in FIG. 13, the field 450 in which characters can be displayed or characters can be input is displayed on the display 150. In a case where the designated position 420 is designated by the straight lines 421, 422, 423 in the reference image 440, the image generator 140 may displays the designated position 420, which has been designated, by coordinate values in the three dimensional orthogonal coordinate system displayed by the marker 430 in the field 450. As a result, the positional accuracy of the designated position 420 which is input by using the straight lines 421, 422, 423 in the reference image 440 is improved. Therefore, observation of the three dimensional images by the microscope can become easier.

In addition, in a case where the accepting unit 130 has accepted the coordinate values input to the field 450 by the keyboard and the like as the input device 120, the image generator 140 may reflect the input coordinate values on the position of the straight lines 421, 422, 423 of the reference image 440. As a result, the positional accuracy of the designated position can be improved, and fine adjustment of the designated position 420 becomes easy. Therefore, observation of the three dimensional images by the microscope can become easier.

Note that, in the aforementioned example, the accepting unit 130 has accepted input of rotation via the key 510 displayed on the display 150. However, the key 510 may not be used. For example, in a case where the mouse is dragged in a state in which the mouse cursor is positioned within the region where the display microscope image 334 is displayed on the display 150, the input of rotation corresponding to the drag operation may be accepted. For example, in a case where the accepting unit 130 has accepted an operation of dragging (in the −Z direction) the position above (+Z direction) the display microscope image 321 and pulling it down, the image generator 140 generates a new display microscope image 334 corresponding to the case where the three dimensional microscope image 310 is rotated about the Z axis. As a result, by more intuitively operating the input of the three dimensional microscope image 310 and three dimensional magnified image 340 in the observation direction, the observation of the three dimensional images by the microscope can become easier.

Figure 14:
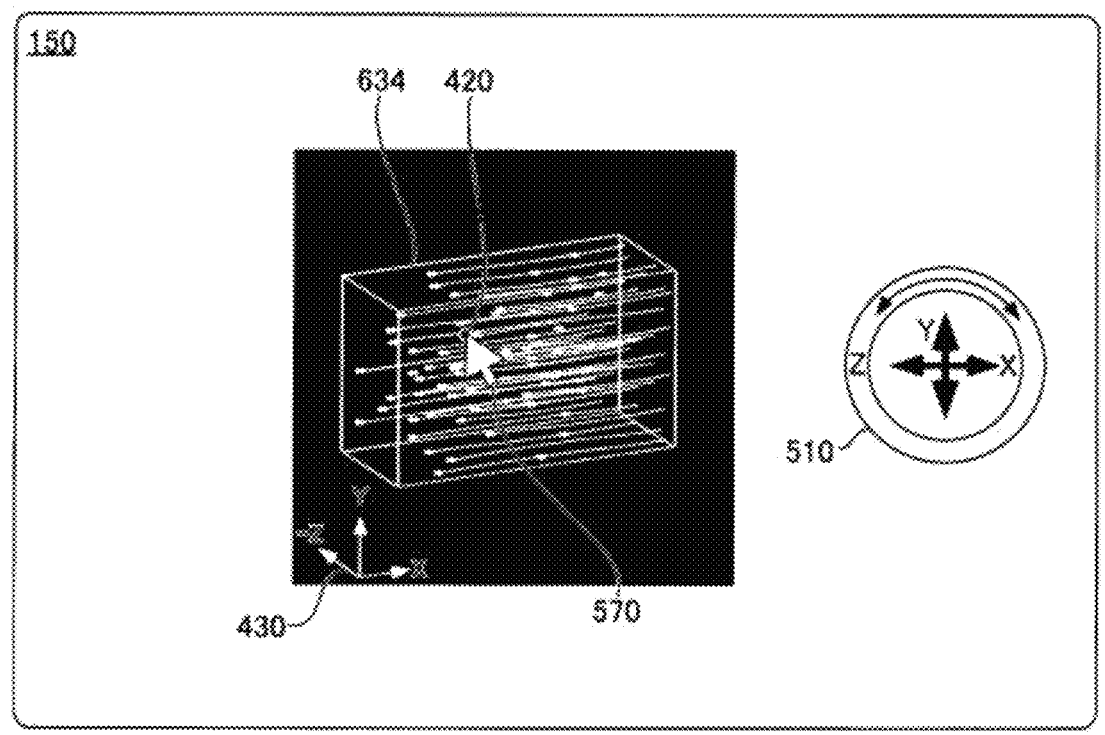
FIG. 14 is a diagram illustrating an image displayed on the display 150.

FIG. 14 is a diagram configured to describe another modification of an operation of designating the designated position 420 in the image processor 101 via the input device 120. FIG. 14 illustrates an image displayed on the display 150.

In the example illustrated in FIG. 14, in step S102 of FIG. 11, the image generator 140 generates the microscope image 634 for position designation and displays it on the display 150 (step S103 in the same diagram). In addition, the image generator 140 displays the key 510 on the side of the microscope image 634.

The microscope image 634 illustrated in FIG. 14 is generated by the image generator 140 by projecting the three dimensional microscope image data 310 onto the projection plane 322 similarly to the description with reference to FIG. 5. Here, by accepting an operation of the accepting unit 130 of pressing the key 510 with a mouse, the image generator 140 generates a new display microscope image 324 and displays the display microscope image 324 on the display 150 similarly to the description in FIG. 9. The display microscope image 324 is obtained by projecting the three dimensional microscope image 310 onto the projection plane 322 in a case where the tilt of the three dimensional microscope image 310 illustrated in FIG. 5 with respect to the projection plane 322 is virtually changed. As a result, a state in which the three dimensional microscope image 310 rotates and the observation direction is changing is displayed on the display 150.

In the microscope system 100, the cursor 570 is moved to a desired position of the microscope image 634 by operating the mouse with respect to the aforementioned microscope image 634, and furthermore, the mouse is clicked at the position. Here, the accepting unit 130 identifies the position (XY coordinate) in the microscope image 634 of the specimen designated by the position of the cursor 570 at the point when the mouse is clicked. In addition, since the microscope image 634 is generated based on the three dimensional microscope image data 310, the accepting unit 130 identifies the position in the Z direction (the position in the depth direction) of the specimen designated by the position of the cursor 570 according to the relationship between the position of the specimen of the microscope image 634 and the position of the specimen of the three dimensional microscope image 310. To virtually describe it, the accepting unit 130 accepts a position of a foremost pixel in a direction orthogonal to the plane on which the microscope image 634 is formed, at the position of the cursor 570 at the point when the mouse is clicked, as the designated position 420, wherein the foremost pixel is one of the pixels existing in the direction and having intensity values equal to or larger than a predetermined threshold in the three dimensional microscope image data 310. Thus, in the microscope system 100, since the designated position 420 can be designated intuitively by a simple procedure, the observation of the three dimensional images by the microscope becomes easy.

Note that, in the aforementioned example, the accepting unit 130 accepted the input of the observation direction via the key 510 displayed on the display 150. However, the key 510 may not be used. For example, in a case where the mouse is dragged in a state in which the mouse cursor is positioned within the region where the microscope image 634 is displayed on the display 150, the input of the observation direction corresponding to the drag operation may be accepted. For example, in a case where the accepting unit 130 accepted an operation of dragging (in the −Z direction) the position above (+Z direction) the microscope image 634 and pulling it down, the image generator 140 generates a new microscope image 634 by projecting the three dimensional microscope image 310 onto the projection plane 322 in a case where the tilt of the three dimensional microscope image 310 illustrated in FIG. 5 with respect to the projection plane 322 is virtually changed around the X axis orthogonal to the Z axis. As a result, by more intuitively operating the input of the observation direction of the three dimensional microscope image 310, the observation of the three dimensional images by the microscope can become easier.

Note that, a three dimensional image in which the user feels a three dimensional effect due to parallax and the like may be used instead of using a two-dimensional microscope image for position designation. In addition, a three dimensional magnified image in which the user feels a three dimensional effect due to parallax and the like may be displayed instead of displaying the magnified image 341. In this case, a three dimensional display such as a VR head mounted display, VR goggle, naked eye 3D monitor, 3D hologram and the like is used as the display 150 configured to display the three dimensional image and the three dimensional magnified image. In addition, in a case where the three dimensional display is used as the display 15, a pointing device such as a 3D mouse (3Dconnexion (registered trademark)) or a motion sensor device (Kinect (registered trademark), LEAP (registered trademark) and the like) and the like may be used instead of or in addition to the mouse.

In this case, instead of step S102 in FIG. 11, the image generator 140 generates a three dimensional image for position designation based on the three dimensional microscope image data 310, and displays the three dimensional image on a three dimensional display instead of step S103. In step S104, the accepting unit 130 accepts designation of a position in the three-dimensional three dimensional image from the user via the pointing device, and sets it as the designated position. The image generator 140 generates three dimensional magnified image data in which the region including the designated position is magnified in step S105 and generates a three dimensional magnified image based on the three dimensional magnified image data instead of step S106 and displays the three dimensional magnified image on the three dimensional display instead of step S107. As a result, since the user directly uses a three dimensional image that feels a three dimensional effect, designation of the three dimensional microscope image data to be magnified becomes easy, and the three dimensional magnified image is displayed on the three dimensional display, thus observation of magnified portion become easy. Therefore, a series of observation in the three dimensional microscope images can be performed more easily.

Note that, in any of the aforementioned embodiments, the two-dimensional display microscope image 321 is generated from the three dimensional microscope image data 310, and the two-dimensional display reference image 440 is generated from the reference image data and displayed on the display 150. Instead, the display microscope image 321 and the display reference image 440 may be three dimensionally displayed on the three dimensional display.

In addition, in any of the aforementioned embodiments, the accepting unit 130 accepts designation of at least a part of the three dimensional microscope image data 310 by designation of the position in the microscope image, but the designation method is not limited to this. The accepting unit 130 may accept designation of a region of three dimensional space of the three dimensional microscope image data 310 instead of designation of the position as designation of at least a part of the three dimensional microscope image data 310. In this case, for example, in the two-dimensional microscope image, when the user moves while dragging the mouse at a certain position, a rectangle whose diagonal line is the movement amount may be displayed, and the rectangle may be accepted by the accepting unit 130 by releasing the drag. Then, the image generator 140 acquires information (for example, the coordinates of four vertices of the rectangle) regarding the position of the designated rectangle from the accepting unit 130, the image generator 140 identifies a preset region including the designated rectangle (for example, a region whose diameter is the diagonal line of the designated rectangle) as a region to be magnified based on this information. In addition, the accepting unit 130 may accept the coordinates of the three dimensional microscope image 310 (the three dimensional microscope image data 310) directly input by the keyboard and the like as the input device 120 as the position information. In this case, coordinates of one point may be accepted to designate a point on the three dimensional microscope image 310, or coordinates of a plurality of points (for example, coordinates of four vertices in the case of a rectangular region) may be accepted to designate a region on the three dimensional microscope image 310. The image generator 140 acquires the accepted coordinates and identifies a region including the point and the region corresponding to the coordinates as a region to be magnified. Further, the accepting unit 130 may accept designation of the region itself to be magnified by the three dimensional microscope image 310. In this case, in the three dimensional microscope image 310, a circle whose diameter or radius is the movement amount is displayed by moving while dragging the mouse at a certain position, and the circle may be accepted as a region to be magnified by releasing the drag. Then, the image generator 140 acquires information (for example, the center coordinates and the radius of the circle) regarding the position of the designated circle, and identifies the designated circle as a region to be magnified. In any of the aforementioned cases, designation of the region is not limited to a rectangle or a circle, and may be designated in other shapes.

Figure 15:
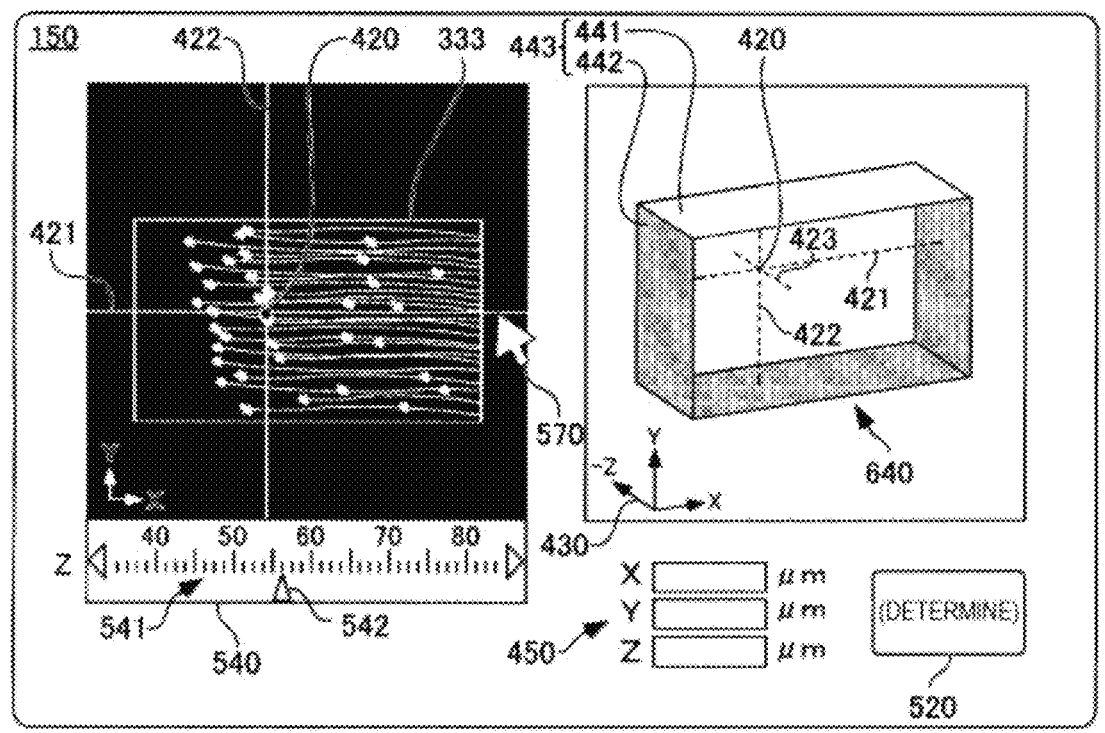
FIG. 15 is a diagram illustrating an image displayed on the display 150.

FIG. 15 is a diagram configured to describe another modification of an operation of designating the designated position 420 in the image processor 101 via the input device 120. FIG. 15 illustrates an image displayed on the display 150.

In the example illustrated in FIG. 15, in step S103 of FIG. 11, the image generator 140 displays a same image as the microscope image 333, the slider 540 and the button 520 illustrated in FIG. 12 on the left side of the display 150 in the diagram. In addition, the image generator 140 displays the position reference image 640, the field 450, and the button 520 on the right side of the display 150 in the diagram. The position reference image 640 may be the same type as the three dimensional magnified image data 340 of FIG. 13.

Similarly to FIG. 12, the position is designated (step S104 in FIG. 11) by the user operating the straight lines 421 and 422 displayed on the microscope image 333 in an overlapping manner and the slider 540 displayed adjacent to the bottom of the microscope image 333 with the mouse as the input device 120. The accepting unit 130 accepts designation of the designated position 420 by pressing down the button 520.

Further, the image generator 140 identifies a region including the designated position 420 in the three dimensional microscope image 310, and generates the three dimensional magnified image data 340 in which the region is magnified (step S105 in FIG. 11). Further, the image generator 140 generates the magnified image 341 to be displayed on the display 150 (step S106 in FIG. 11), and displays the magnified image 341 on the display 150 (step S107) based on the three dimensional magnified image data 340.

Here, in the example illustrated in FIG. 15, the image generator 140 moves the straight lines 421 and 422 displayed in the position reference image 640 interlocked with the movement of the straight lines 421 and 422 in the microscope image 333. As a result, the user can confirm the position of the designated position 420 in which the user himself moved on the side of the microscope image 333 in real time in the position reference image 640.

As a result, the confirmation of the designated position 420 becomes easy in a case where designating the designated position 420 and also improves the positional accuracy of the designated position 420. Therefore, the observation of the three dimensional images by the microscope becomes easy.

In addition, in the example illustrated in FIG. 15, the field 450 in which characters can be displayed or characters can be input is displayed on the display 150. In a case where the designated position 420 is designated in the microscope image 333, the image generator 140 may display the designated position 420, which has been designated, with coordinate values in the three dimensional orthogonal coordinate system displayed by the marker 430 in the field 450. As a result, the positional accuracy of the designated position 420 which is input by using the straight lines 421, 422, 423 in the position reference image 640 is improved. Therefore, the observation of the three dimensional images by the microscope can become easier.

Further, in a case where the accepting unit 130 accepted the coordinate values input to the field 450 by the keyboard and the like as the input device 120, the image generator 140 may reflect the input coordinate values on the position of the straight lines 421, 422, 423 of the position reference image 640. As a result, the positional accuracy of the designated position can be improved, and fine adjustment of the designated position 420 becomes easy. Therefore, observation of the three dimensional images by the microscope can become easier.

In any of the aforementioned embodiments and modifications, the magnified image 341 is an image generated by projecting at least a part of the three dimensional magnified image 340 onto an arbitrary plane. Instead, the magnified image 341 may be an image appearing in the cross section of the three dimensional magnified image 340. Further, the magnified image 341 may be generated by another existing method of generating a two-dimensional image from the three dimensional magnified image data 340 which is three dimensional image data.

Similarly, in any of the aforementioned embodiments and modifications, the display microscope image 321 is an image generated by projecting at least a part of the three dimensional microscope image 310 onto an arbitrary plane. Instead, the display microscope image 321 may be an image appearing in the cross section of the three dimensional microscope image 310. Further, the display microscope image 321 may be generated by another existing method of generating a two-dimensional image from the three dimensional microscope image data 310 which is three dimensional image data.

Figure 16:
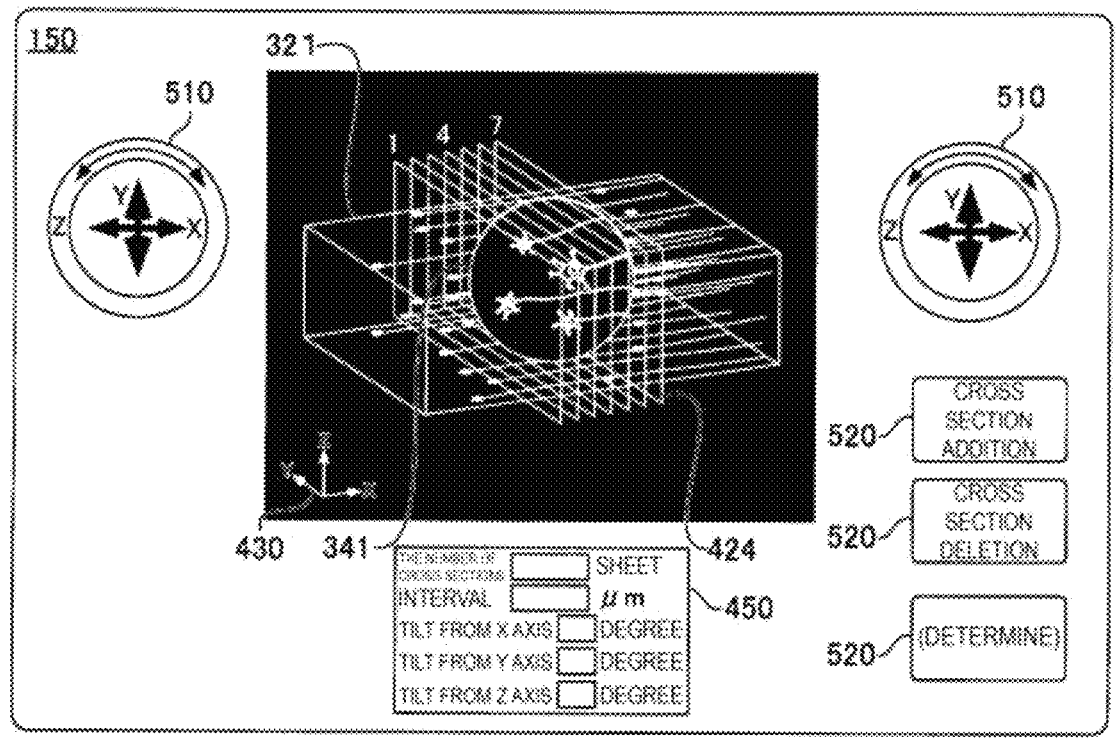
FIG. 16 is a diagram illustrating an image displayed on the display 150.

FIG. 16 illustrates a modification (a modification of steps S106 and S107 in FIG. 11) of the display microscope image and the magnified image displayed on the display 150. In the example of FIG. 16, the accepting unit 130 accepts the position of the cross section of the three dimensional magnified image data 340. In addition, the image generator 140 outputs the cross-sectional image at the designated position in the three dimensional magnified image data 340 as a two-dimensional image.

The image generator 140 displays the display microscope image 321, the magnified image 341, a plane designation display 424, the key 510, the button 520, and the field 450 on the display 150. The magnified image 341 is displayed on the display microscope image 321 in an overlapping manner.

The image generator 140 displays the display microscope image 321 with the designated tilt by operating the key 510 on the left side in the diagram with the mouse. In addition, the image generator 140 displays the magnified image 341 on the display 150 with the designated tilt in accordance with the operation of the key 510 on the right side in the diagram with the mouse.

Further, the image generator 140 displays the plane designation display 424 in an overlapping manner on the magnified image 341 in accordance with the numerical input to the field 450 or the operation of the cross section addition button 520 by the mouse. In addition, the image generator 140 moves the plane designation display 424 on the screen by a mouse dragging operation to arrange the plane designation display 424 at a position where a desired cross section can be obtained. Further, the image generator 140 changes the tilt of the plane designation display 424 in accordance with the operation of the mouse with respect to the key positioned on the right side in the diagram. Thus, in a case where the plane designation display 424 coincides with the desired cross section, one of the buttons 520 is pressed with the mouse to fix the position of the plane designation display 424.

Hereinafter, the aforementioned operation is repeated until all of the planned cross sections are designated, and the positions and the tilts of a plurality of cross sections are designated for the three dimensional magnified image data 340. In the image processor 101, it is also possible to designate the tilt of the cross section, the number of sheets and the like by inputting a numerical value to the field 450 in addition to the plane designation display 424 by operating the mouse as described above. The numerical value input to the field 450 may be a relative value without a unit or an actual size in a specimen.

Note that, in the aforementioned example, instructions of rotation of the display microscope image 321 and the plane designation display 424 are input by operating the mouse via the key 510 displayed on the display 150. However, even if the key 510 is not explicitly displayed on the display 150, the display microscope image 321 or the plane designation display 424 may be an interface that rotates following the movement direction of the cursor 570 by dragging the mouse in a state in which the cursor 570 is positioned within the region where the display microscope image 321 or the plane designation display 424 is displayed. As a result, the observation of the three dimensional images by the microscope can become easier by more intuitively operating the rotation of the display microscope image 321 and the plane designation display 424 displayed on the display 150.

Figure 17:
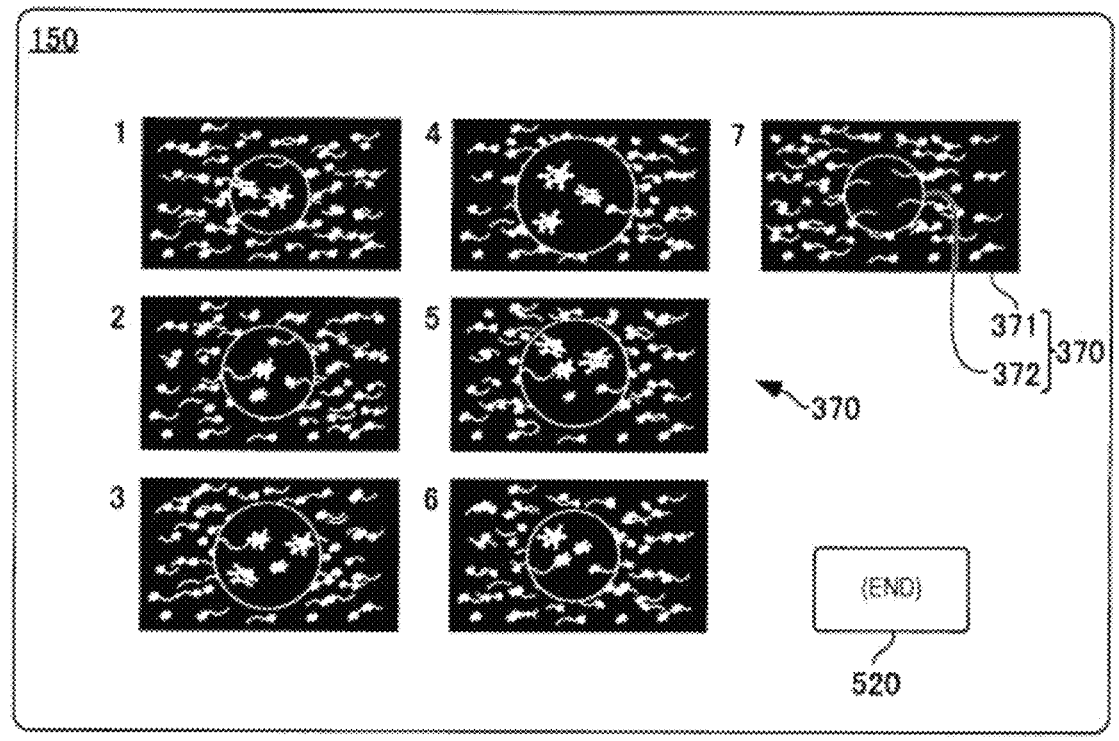
FIG. 17 is a diagram illustrating an image displayed on the display 150.

FIG. 17 illustrates an image that the image generator 140 executes image processing and outputs it to the display 150 after the arrangement of the plane designation display 424 is completed, as described above. On the display 150, a plurality of cross-sectional images 370 in which the cross-section designated by the plane designation display 424 appeared in the image illustrated in FIG. 16 is displayed.

Each of the cross-sectional images 370 includes a display cross-sectional image 371 and a display magnified cross-sectional image 372, respectively. The display cross-sectional image 371 is an image that appears on the cross section by cutting the three dimensional microscope image data 310 that is the basis in a case where generating the display microscope image 321 illustrated in FIG. 16 by the plane designation display 424. In addition, the display magnified cross-sectional image 372 is an image that appears on the cross section by cutting the three dimensional magnified image data 340 that is the basis in a case where generating the magnified image 341 illustrated in FIG. 16, by the plane designation display 424. The image generator 140 superimposes the display cross-sectional image 371 and the display magnified cross-sectional image 372 appearing on each cross-section designated by the plane designation display 424 to generate the cross-sectional image 370.

In this way, in the microscope system 100, it is possible to output an image of the cross section generated on the plane of the position to the display 150 by designating the position of the plane by the arrangement of the plane designation display 424. As a result, the inside of the three dimensional microscope image data 310 can be easily observed in any cross section. Therefore, the observation of the three dimensional images by the microscope becomes easy.

Figure 18:
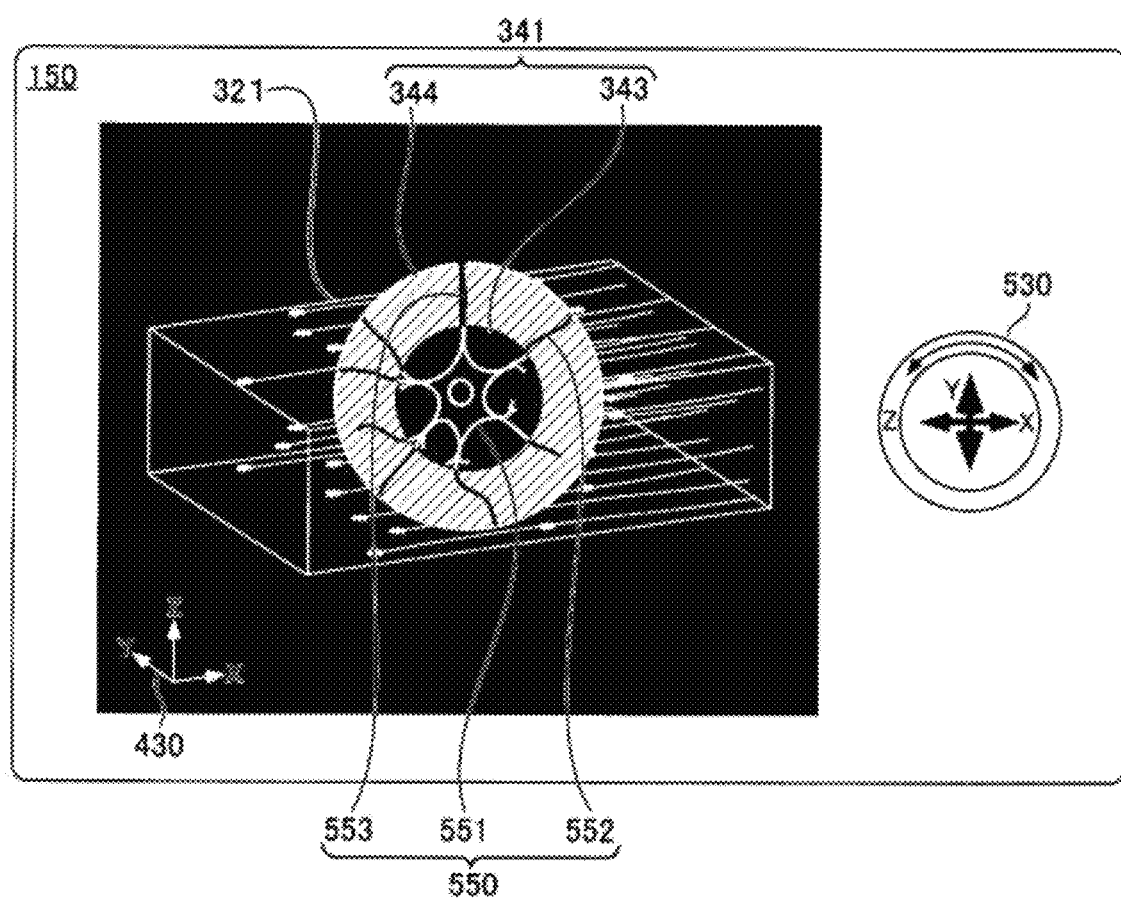
FIG. 18 is a diagram illustrating an image displayed on the display 150.

FIG. 18 is a diagram illustrating an image displayed on the display 150 after executing other processing by the image processor 101. Here, the processing executed by the image generation 140 is a processing configured to generate a first image 343 displayed in a first region including the center of the magnified image 341 and a second image 344 displayed in a second region positioned outside the first region together, in a case where the magnified image 341 is generated from the three dimensional magnified image data 340.

In the illustrated example, three dimensional magnified image data of a nerve cell 550 in which the corresponding region of the three dimensional magnified image data 340 is magnified is generated as the first image 343 output by the image generator 140. The nerve cell 550 include a massive cell body 551, dendrites 552 protruding in the vicinity of the cell body 551, and an axon 553 extending long from the cell body 551.

Here, the image generator 140 generates the first image 343 as a display microscope image mainly including the cell body 551. In addition, the image generator 140 generates the second image 344 which is formed in the region around the first image 343 and includes the dendrites 552.

Here, the first image 343 is a magnified image of the cell body 551 included in the three dimensional magnified image data 340 as it is. The second image 344 is generated as an image in which the dendrites 552 protruding around the cell body 551 is emphasized in a corresponding region of the three dimensional magnified image data 340. In other words, in the second image 344, it can be said that the display of elements other than the dendrites 552 is suppressed. As a result, in a case where the image generator 140 generated the magnified image 341 from the three dimensional magnified image data 340, as illustrated in FIG. 18, the second image 344 in which the radially extending dendrites 552 are emphasized is displayed around the cell body 551 of the nerve cell displayed in the first image.

As a result, also in the magnified image 341, it can be sensuously grasped that the dendrites of the nerve cell are spreading to the surroundings, and contact state between the nerve cell as the object of interest and an adjacent cell (adjacent structure), connection state and the like becomes easy to understand. Therefore, the observation of the three dimensional images by the microscope becomes easy.

Note that, that the object emphasized in the second image 344 is not limited to the one which is connected between the first region and the second region like the dendrites 552. As another example, it may be an object such as a cell which is commonly included in each of the first region and the second region and is discretely present. In addition, emphasis of a particular object in the second image 344 maybe an example that the display condition differs from that of the first image 343, and display conditions other than the emphasis may be different.

Note that, in the aforementioned example, instructions of rotation of the display microscope image 321 and the magnified image 341 are input by operating the mouse via the key 510 displayed on the display 150. However, even if the key 510 is not explicitly displayed on the display 150, the display microscope image 321 or the magnified image 341 may be an interface that rotates following the movement direction of the cursor 570 by dragging the mouse in a state in which cursor 570 is positioned within the region where the display microscope image 321 or the magnified image 341 is displayed. As a result, the observation of the three dimensional images by the microscope can become easier by more intuitively operating the rotation of the display microscope image 321 and the magnified image 341 displayed on the display 150.

Figure 19:
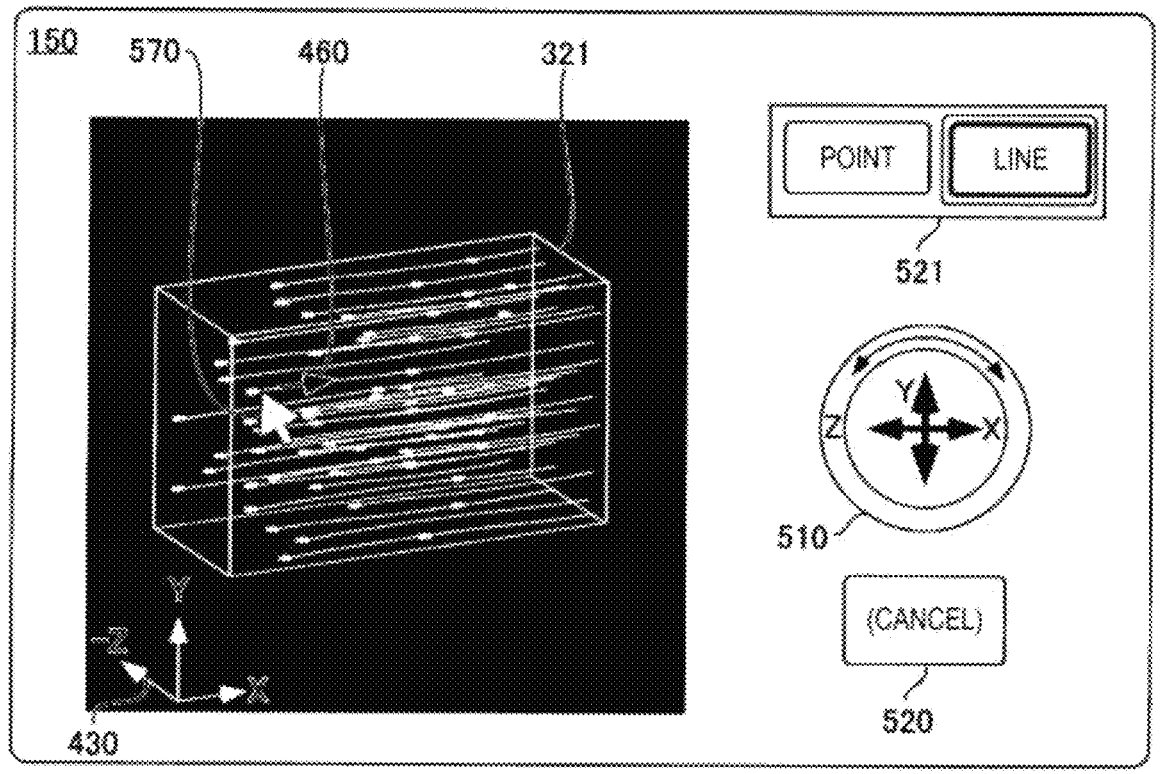
FIG. 19 is a diagram illustrating an image displayed on the display 150.

FIG. 19 is a diagram configured to describe the processing in a case of performing trace observation in which a field of view is moved along a long specimen, step by step. In this example, the nerve cell connected to a long axon is a target of observation.

The image generator 140 generates the three dimensional microscope image data 310 based on the image data 410 acquired from the microscope 110 and generates the display microscope image 321 by projecting the generated three dimensional microscope image data 310 onto the projection plane 322. The display microscope image 321 generated in this manner is output from the image generator 140 to the display 150 and displayed. As a result, as illustrated in the diagram, the display microscope image 321 including the long axon is displayed on the display 150.

The display microscope image 321 displayed on the display 150 can be observed from an arbitrary angle on the screen of the display 150 by operating the key 510 through the mouse. Therefore, it is possible to display the display microscope image 321 with a position and a tilt where the nerve cell with the axon to be observed is easy visible.

In the microscope system 100, the start position of the trace observation is designated by operating the mouse with respect to the display microscope image 321 displayed on the display 150. Note that, the microscope 110 implements two methods as an input method of a trace line 461. As one of the method of forming the trace line 461, there is a method of designating a trace line with a continuous line drawn by a mouse drag operation. In addition, there is a method of designating the positions of a plurality of points on the route of the trace line 461 and complementing the trace line among a plurality of points in the image processor 101.

In the microscope system 100, both of the aforementioned two methods are implemented, and they can be selected and selectively used according to the application. In the illustrated example, it is selected to continuously input the trace line 461 by a line, that is, a mouse drag operation with the button 521 on the upper right of the display image of the display 150.

In this case, first, the user presses down the mouse button in a state in which the cursor 570 is in contact with the start position of the observation and moves the cursor 570 along the axon of the nerve cell serving as the target of the observation by a drag operation that moves the mouse while pressing down the button. As a result, the trace line 461 serving as the route of trace is displayed in an overlapping manner on the display microscope image 321 displayed on the display 150 by the image generator 140 until the mouse button is released. The other method will be described later with reference to FIG. 23.

Figure 20:
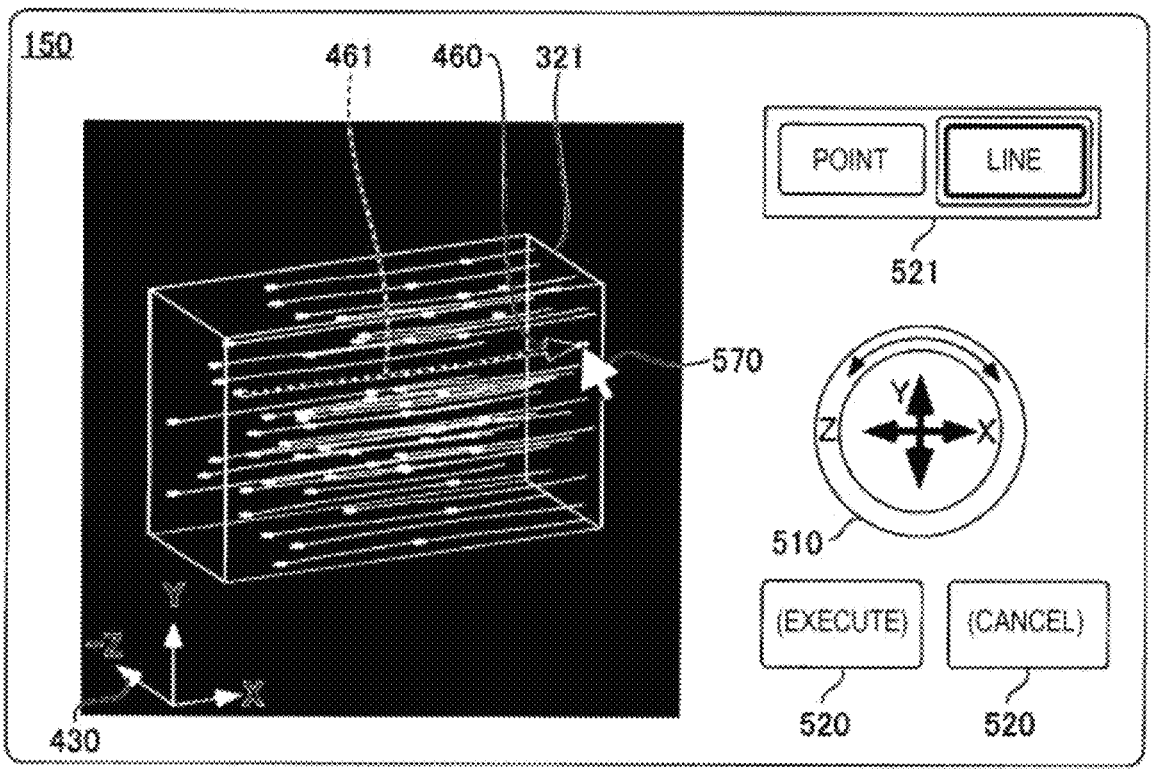
FIG. 20 is a diagram illustrating an image displayed on the display 150.

FIG. 20 is a diagram configured to describe steps following the aforementioned operation. As indicated by an arrow 460 in the diagram, when the cursor 570 reaches the end of the observation range by dragging the mouse, the user determines the input of the designation of the observation range as the display microscope image 321 by releasing the mouse button. As a result, designation of the start position and the end position of the observation is accepted by the accepting unit 130, and the image generator 140 superimposes the trace line 461 drawn as a trajectory of the cursor 570 in superposition with a video image of the designated axon, on the microscope image 321 and displays it on the display 150.

Figure 21:
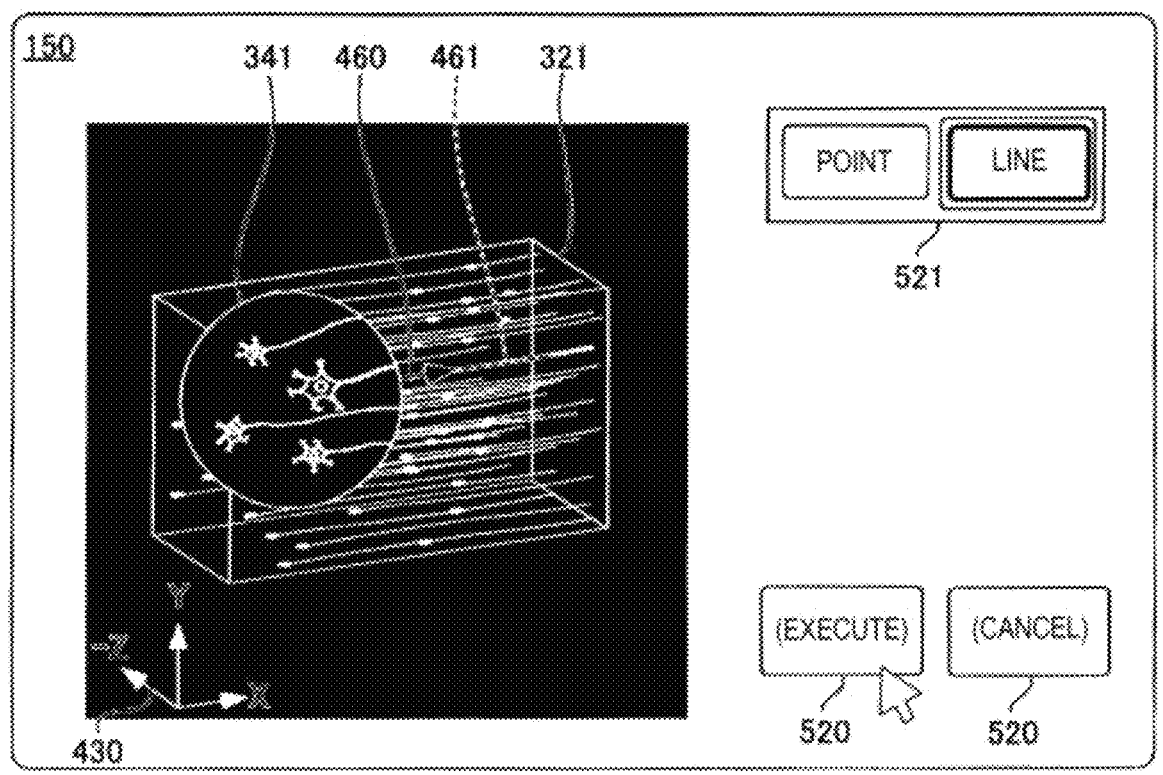
FIG. 21 is a diagram illustrating an image displayed on the display 150.

FIG. 21 is a diagram configured to describe a processing executed by the image processor 101 following the aforementioned operation. As illustrated in the diagram, when the execution button 520 is pressed with the mouse operated by the user after the position at which the magnified image is generated is designated as the trace line, the image generator 140 first acquires the start position of the trace line 461 as the first designated position 420 and generates the three dimensional magnified image data 340 based on the three dimensional microscope image data 310. Next, the image generator 140 generates the magnified image 341 from the generated three dimensional magnified image data 340.

The magnified image 341 generated in this manner is displayed in a superimposed manner on the display microscope image 321 such that its center coincides with the start point of the trace line 461 in the display microscope image 321. Further, when the magnified image 341 is output to the display 150, the image generator 140 selects a point closer to the end side on the trace line 461, and generates a next three dimensional magnified image data 340 around the position.

On the display 150, the magnified image 341 are sequentially displayed toward the end along the trace line 461 by repeating a series of image processing from the acquisition of a new designated position on the trace line to the display of the magnified image 341 as described above. As a result, the axon 553 having a length larger than the field of view of the magnified image 341 can be traced and continuously observed. As a result, it is possible to easily execute observation that achieves both a high resolution of the microscope and a continuous observation of a long specimen.

Note that, in the aforementioned example, an instruction of rotation of the display microscope image 321 was input by operating the mouse via the key 510 displayed on the display 150. However, even if the key 510 is not explicitly displayed on the display 150, the display microscope image 321 may be an interface that rotates following the movement direction of the cursor 570 by dragging the mouse in a state in which the cursor 570 is positioned within the region where the display microscope image 321 is displayed. As a result, the observation of the three dimensional images by the microscope can become easier by intuitively operating the rotation of the display microscope image 321 displayed on the display 150.

Figure 22:
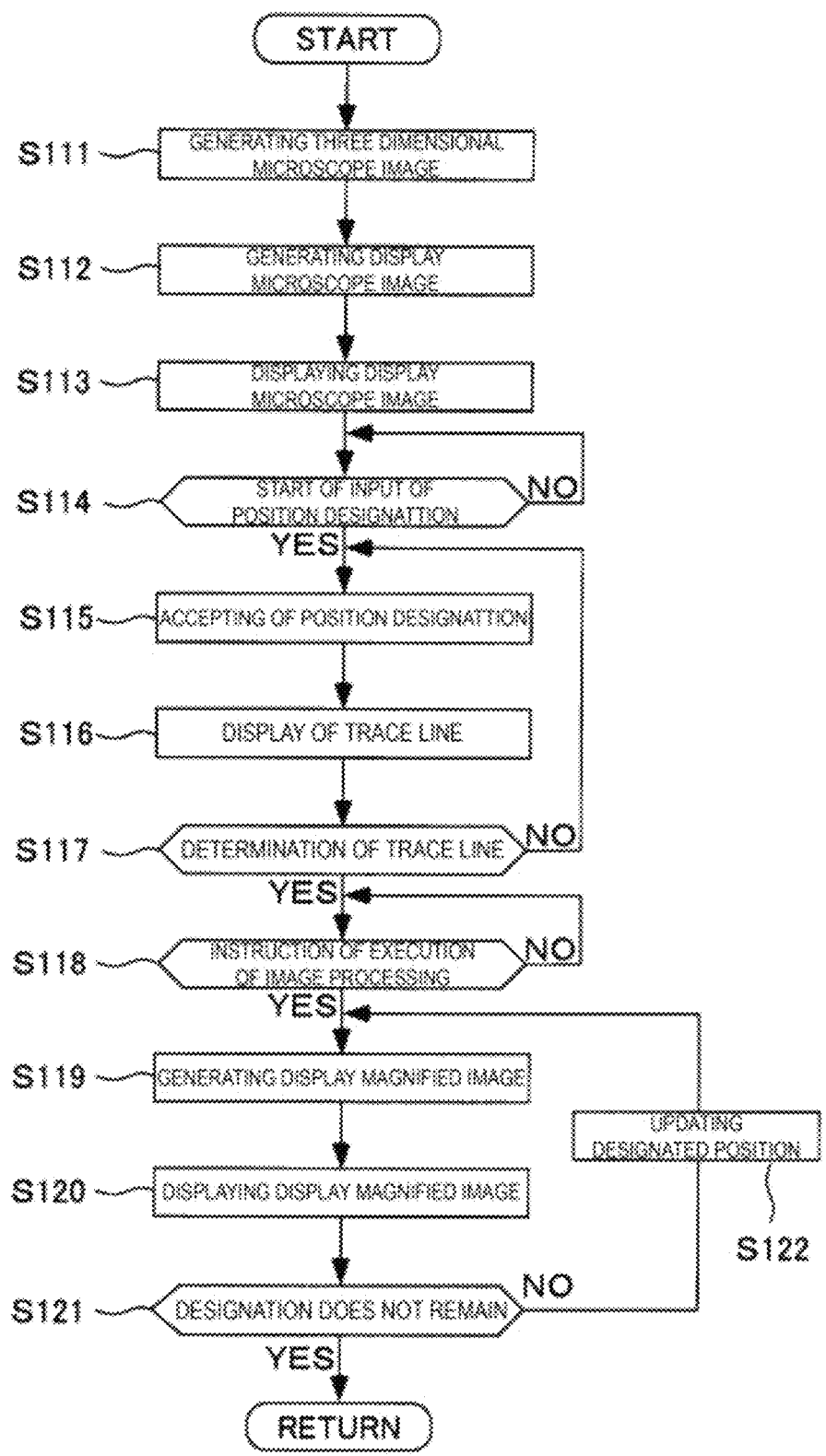
FIG. 22 is a flowchart of a processing executed by the image processor 101.

FIG. 22 is a flowchart illustrating a procedure of processing by the image processor 101 described with reference to FIG. 19 to FIG. 21. When an image processing by the image processor 101 is started, first, the image generator 140 generates the three dimensional microscope image data 310 based on a plurality of the image data 410 acquired from the microscope 110 as illustrated in FIG. 2 and FIG. 3 (step S111).

Next, the image generator 140 generates a microscopic image based on the three dimensional microscope image data 310 (step S112), and displays it on the display 150 (step S113). Note that, in this example, the display microscope image 321 generated by projecting the three dimensional microscope image data 310 onto the projection plane 322 is generated (step S111) and displayed on the display 150 (step S113).

Next, the image generation unit 140 waits (step S114: NO) while the accepting unit 130 monitors that the user inputs the trace line 401 to the display microscope image 321 displayed on the display 150 as the input of the position designation. When the user inputs the trace line 461 as input of the position designation (step S114: YES), the accepting unit 130 accepts the input trace line (step S115) and causes the image generator 140 to refer to the trace line.

Next, the image generator 140 sequentially displays the trace line 461 on the display 150 by overlapping on the display microscope image 321 (step S116) based on the acquired trace line 461. Thereafter, while the drag operation of the mouse is continuing, the image generator 140 serves to extend the trace line 461 displayed on the display 150 (step S117: YES).

Subsequently, when the input of the trace line by the mouse is completed (step S117: YES), the image generator 140 waits while monitoring that the user presses the button 520 for instructing execution (step S118: NO). When the user presses the button 520 by operating the mouse and instructs the start of image processing (step S118: YES), the image generator 140 generates the three dimensional magnified image data 340 from a part of the three dimensional microscope image data 310 (step S119), and generates the magnified image 341 from the generated three dimensional magnified image data 340 (step S120).

Further, the image generator 140 checks whether there remains a position where the magnified image 341 is not generated even though it is designated by the trace line 461 (step S121), and in a case where unprocessed remains at the position on the trace line (step S121: NO), the designated position 420 serving as the target of the processing is updated (step S122), and the steps from step S119 to step S121 are repeated. Then, in a case where the unprocessed position does not remain, the processing is terminated. In this way, the user can easily observe a long specimen such as a filamentous shape by designating a trace route in advance.

Figure 23:
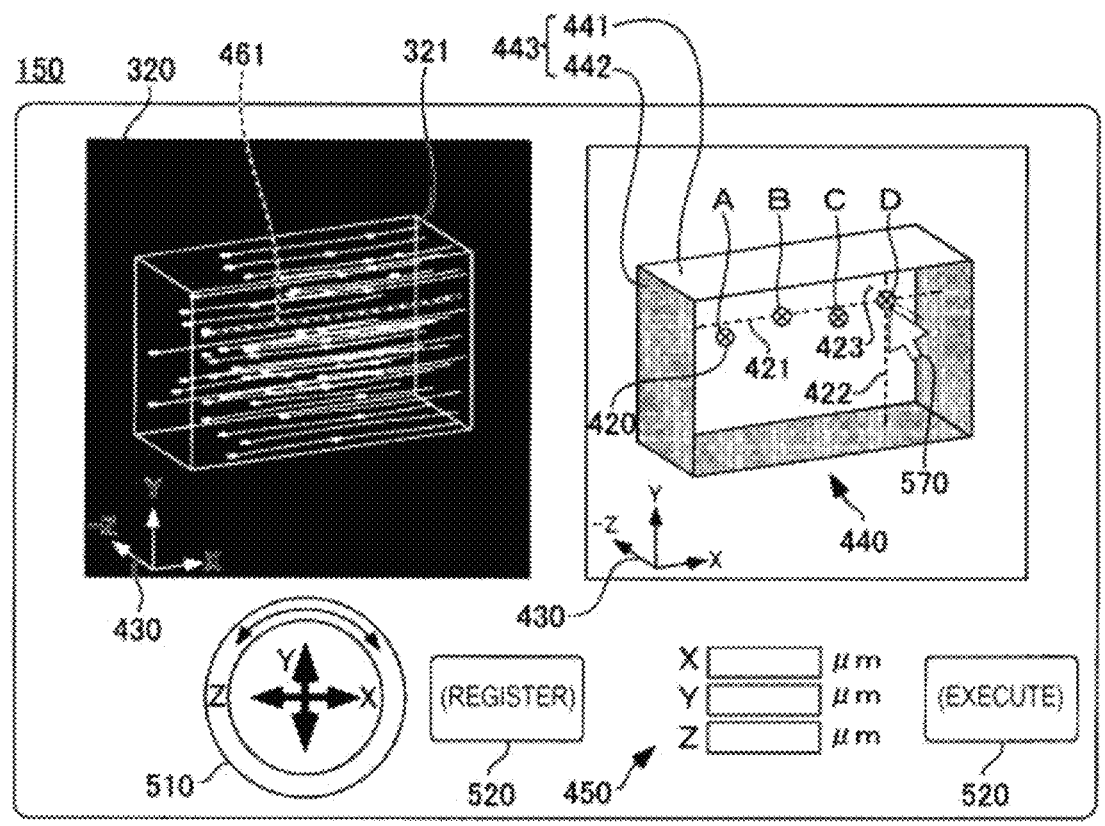
FIG. 23 is a diagram illustrating an image displayed on the display 150.

FIG. 23 is a diagram configured to describe another method in the case of inputting the trace line 461 to the image processor 101. It is possible to input the trace line 461 to the image processor 101 by executing this method in place of the procedure described with reference to FIGS. 19 to 21. First, in the screen illustrated in FIG. 19, a point is selected as input of the trace line 461 by the button 521. As a result, the image illustrated in FIG. 23 is displayed on the display 150.

As illustrated in the diagram, the image generator 140 displays the display microscope image 321 also illustrated in FIG. 9 on the left side of the display 150 in the diagram. In addition, the image generator 140 displays the display reference image 440 also illustrated in FIG. 13 on the right side of the display 150 in the diagram. Further, the image generator 140 displays the key 510, the button 520, and the field 450 in the lower stage of the display 150 in the diagram.

Similarly to the display microscope image 321 illustrated in FIG. 19, the display microscope image 321 illustrated in the diagram can be rotated by operating the key 510 with the mouse. As described with reference to FIG. 9, the display reference image 440 rotates following the rotation in a case where the display microscope image 321 rotated. Therefore, the relative positions of the display microscope image 321 and the display reference image 440 are fixed.

In addition, the straight lines 421, 422, and 423 are displayed inside the display reference image 440. The user can move the position of the intersection within the region of the three dimensional microscope image data 310 by moving two of the straight lines 421, 422, 423 via the operation of the mouse.

Therefore, the user designates a position overlapping with an object to be traced, registers the position 420 as one point on the trace line 461 in the accepting unit 130 by pressing the button 520 for registration by operating the mouse. Thus, the point A of the first trace is held in the image processor 101 by registration.

Further, the accepting unit 130 accepts a plurality of points, in the illustrated example, the positions of trace points B to D by repeating the aforementioned operation. Then, the user presses the button 520 configured to instruct the execution of the trace by operating the mouse, and instructs the image generator 140 to execute image processing after a sufficient number of trace points are registered.

As a result, in the image processor 101, the image generator 140 generates the trace line 461 that passes through a plurality of trace points A to D, and superimposes the trace line 461 on the display microscope image 321 and displays it on the display 150. Moreover, similarly to the case illustrated in FIG. 21, the image generator 140 traces the trace line 461 and moves the magnified image 341 while updating the magnified image 341. In this way, the user continuously observes the entire axon along the designated trace line.

Note that, in the aforementioned example, instructions of rotation of the display microscope image 321 and the display reference image 440 are input by operating the mouse via the key 510 displayed on the display 150. However, even if the key 510 is not explicitly displayed on the display 150, the display microscope image 321 and the display reference image 440 may be an interface that rotates following the movement direction of the cursor 570 by dragging the mouse in a state in which the cursor 570 is positioned within the region where the display microscope image 321 or the display reference image 440 is displayed. As a result, the observation of the three dimensional images by the microscope can become easier by intuitively operating the rotation of the display microscope image 321 and the display reference image 440 displayed on the display 150.

Figure 24:
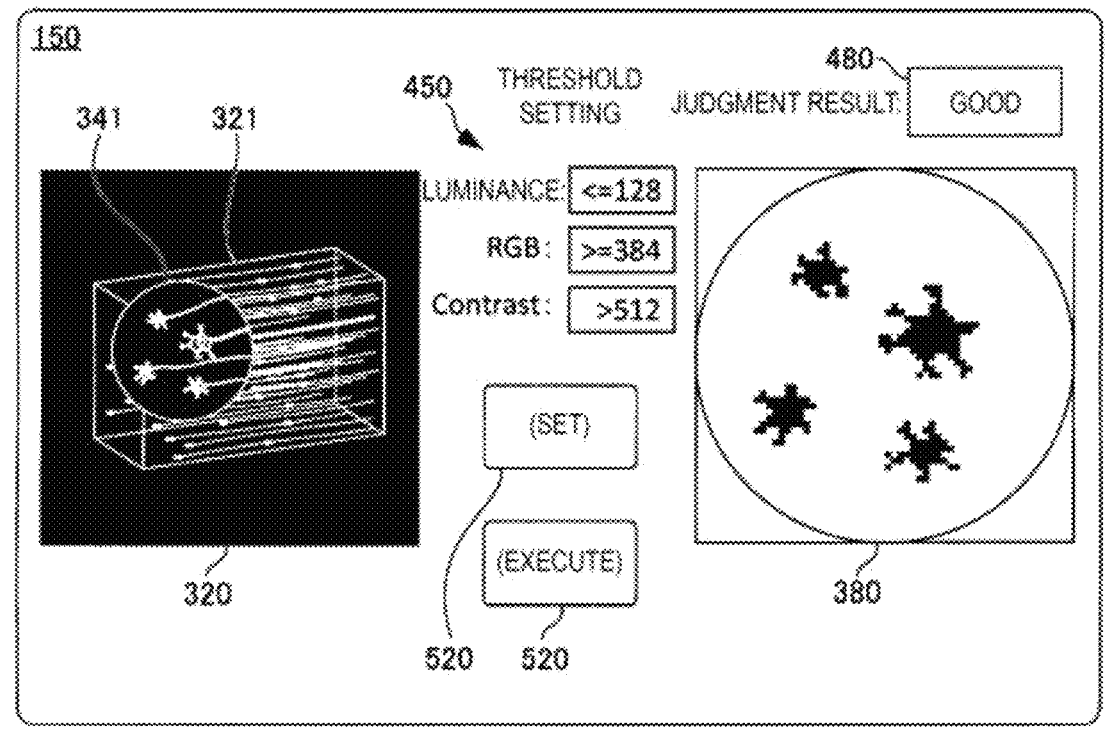
FIG. 24 is a diagram illustrating an image displayed on the display 150.

FIG. 24 illustrates an image displayed on the display 150 in a case where the image processor 101 also executes another processing. The image generator 140 displays the display microscope image 321 in which the magnified image 341 is superimposed on the left side portion in the diagram.

In addition, the image generator 140 displays a binarized image 380 obtained by binarizing the magnified image 341 by image processing on the right side portion in the diagram. Further, in the center of the image, the field 450 configured to display a set threshold by a numerical value and the button 520 configured to instruct setting and execution of processing to be described next are arranged. In addition, a display column 480 configured to display a result of judgment to be described later is arranged above the binarized image 380.

In a case where the illustrated image is displayed on the display 150, the image generator 140 in the image processor 101 has already generated the three dimensional magnified image data 340 corresponding to the input position 420, and furthermore generates the magnified image 341 by projecting the three dimensional magnified image data 340 onto a projection plane parallel to the surface formed by the display microscope image 321.

In the aforementioned state, the user sets the threshold in the image processor 101 by using the mouse and the keyboard. In a case where the threshold is set, the value of the input threshold is displayed in the field 450 by numerical value. The input numerical value is held in the image generator 140 after it is determined by operating the button 520 configured to instruct setting with the mouse and accepted by the accepting unit 130 forming the threshold accepting unit.

Next, when the user operates the mouse to press the button 520 configured to instruct execution, the image generator 140 compares the intensity of each pixel forming the three dimensional magnified image data 340 with the threshold, and binarizes it according to whether the threshold has been exceeded. Further, the image generator 140 reconstructs the binarized pixels into the three dimensional magnified image data. Further, for example, the image generator 140 judges whether the quality of the processed three dimensional magnified image data 340 as an image is good, based on the proportion of pixels exceeding the threshold in the reconstructed three dimensional magnified image data 340.

The image generator 140 causes the display 150 to output and display the judgment result. The judgment result is displayed in the display column 480 of the screen displayed on the display 150. In addition, a reconstructed binarized image 380 is also displayed on the same screen. As a result, the user can confirm the validity of the judgment result. In this way, since the image processor 101 can automatically evaluate the three dimensional magnified image corresponding to the position 420, the work of evaluating the microscope image can be saved. Therefore, the observation of the three dimensional images by the microscope becomes easy.

Note that, binarization may be an example of display conditions, and the image generator 140 may output the magnified image to be displayed under different display conditions by a method other than binarization depending on whether the intensity of each pixel exceeds the threshold.

Figure 25:
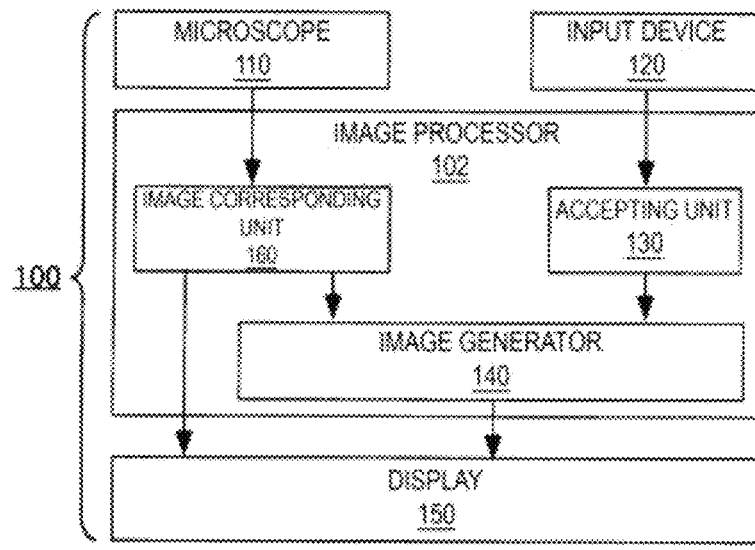
FIG. 25 is a block diagram of the microscope system 100.

FIG. 25 is a block diagram of the microscope system 100 including the image processor 102. In the microscope system 100 illustrated in FIG. 25, the image processor 102 is a section to be described next, which is different from the microscope system 100 illustrated in FIG. 1. In addition, the microscope 111 is also different from the microscope 110 illustrated in FIG. 1. Since the other parts have the same structure as the image processor 101, the same reference numbers are assigned to common elements, and redundant description is omitted.

The image processor 102 is different from the image processor 101 in that the image processor 102 includes an image corresponding unit 160 that accepts an input from the microscope 111 and causes the image generator 140 and the display 150 to acquire the three dimensional microscope image data 310. In addition, in the microscope system 100, the microscope 111 is different from the image processor 101 in that the microscope Ill includes a plurality of microscopes that generate the three dimensional microscope image data 310 from specimens by using mutually different microscopy methods.

In the microscope system 100 as described above, the image corresponding unit 160 of the image processor 102 acquires two three dimensional microscope image data 310 constituted by mutually different microscopy methods from the microscope 111 and executes a processing of associating them with each other. The image correspondence unit 160 associates the pixel position which is the three dimensional coordinate value of each of the pixels constituting one three dimensional microscope image data 310 with the pixel position of the other three dimensional microscope image data 310. Since the pixel position mentioned here is a position inside each three dimensional microscope image data, it can be called an image position.

Figure 26:
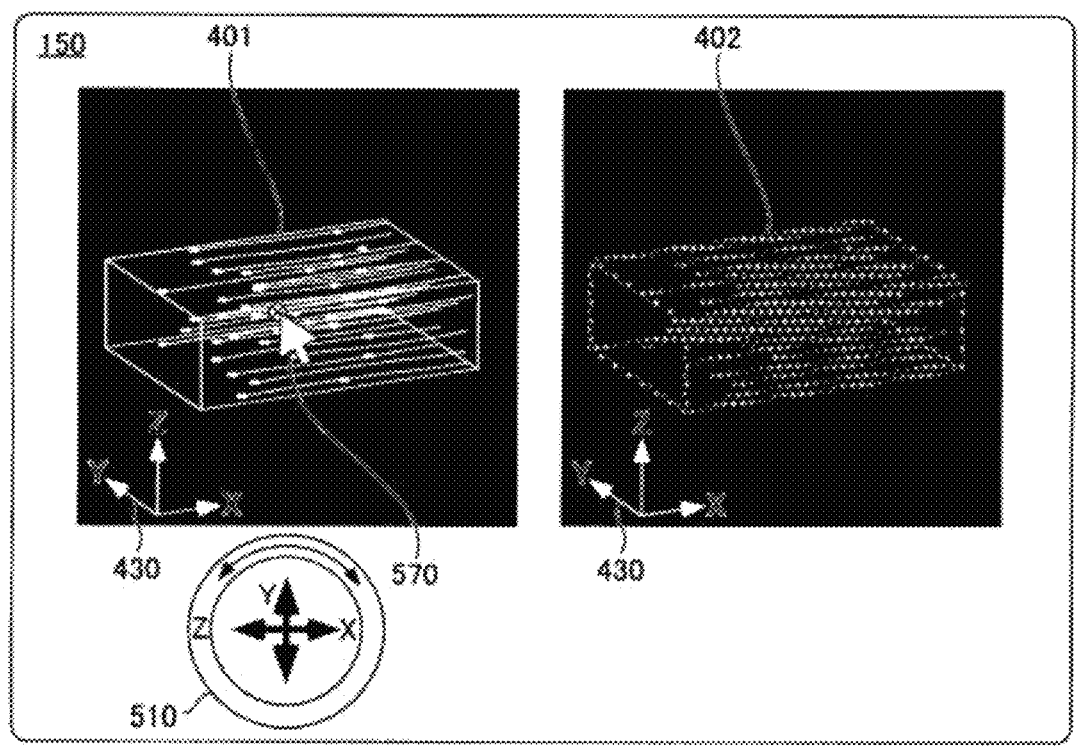
FIG. 26 is a diagram illustrating an image displayed on the display 150.

FIG. 26 illustrates the state in which the first display microscope image 401 and the second display microscope image 402 generated from the two three dimensional microscope image data 310 associated with each other by the image corresponding unit 160 is displayed on the display 150 in juxtaposition.

In the present embodiment, the first display microscope image 401 captures a specimen by SIM (Structured Illumination Microscopy). The SIM can observe the specimen under illumination with a periodic illumination pattern and reconstruct a microscope image representing the microstructure of the specimen smaller than the wavelength of illumination light based on interference fringes generated in the observation image.

In addition, the second display microscope image 402 was generated from the three dimensional microscope image data 310 obtained by capturing the specimen by STochastic Optical Reconstruction Microscopy (STORM). The STORM can reconstruct fluorescent images at a resolution higher than the wavelength of the illumination light by superimposing position information of fluorescent dyes detected with high accuracy from a plurality of fluorescence images.

As described with reference to FIG. 5, each of the first display microscope image 401 and the second display microscope image 402 is generated by projecting the three dimensional microscope image data 310 onto the projection plane and the three dimensional microscope image data 310 is generated by stacking two-dimensional microscope images captured with a plurality of focal planes, respectively, as described with reference to FIG. 2. Further, the first display microscope image 401 and the second display microscope image 402 are associated with the image corresponding unit 160, and the size, tilt, and display position of the image are aligned.

Therefore, the first display microscope image 401 and the second display microscope image 402 at the same size, the same tilt, and the same display position are displayed except for the difference in the texture due to the difference in the microscopy method. In addition, since the first magnified image 403 and the second magnified image 404 are associated with each other, in a case where the first magnified image 403 is updated to the rotated image by the operation of the key 510, the second magnified image 404 is also updated to the display microscope image rotated in the same manner.

Figure 27:
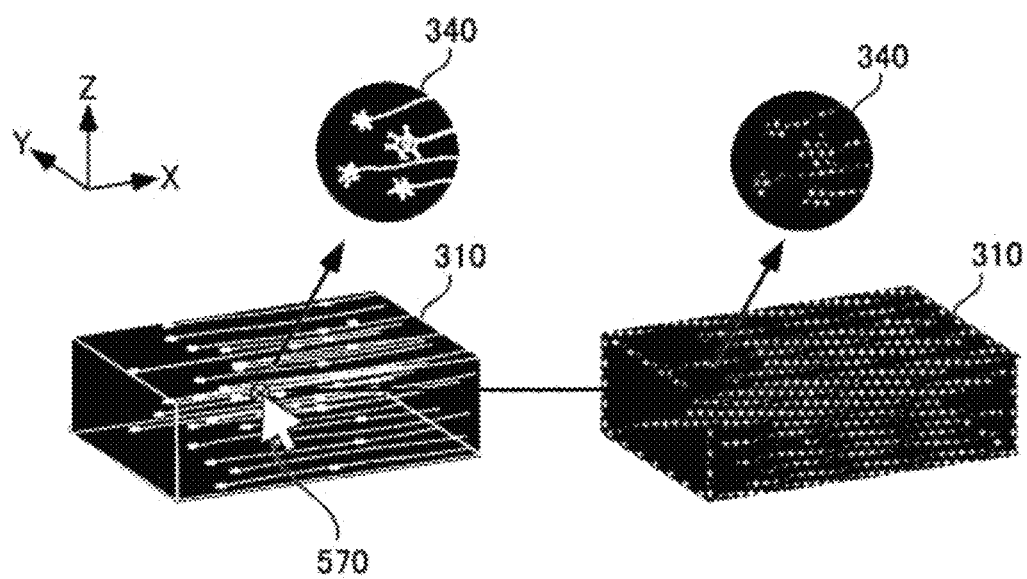
FIG. 27 is a schematic view illustrating a concept of a processing executed by an image processor 102.

FIG. 27 is a diagram configured to describe the concept of a processing executed by the image generator 140. When one position in the three dimensional microscope image data 310 which is the basis of the first display microscope image 401 is accepted by the accepting unit 130 by the cursor 570 operated by the mouse, the image generator 140 identifies the position in the other three dimensional microscope image data 310 corresponding to the accepted position. Further, the image generator 140 identifies a region having a preset size for each of the designated position and the identified position. The region identified in the present embodiment is a region surrounded by a sphere of a predetermined radius around the designated position and the identified position.

Further, the image generator 140 generates the three dimensional magnified image data regarding for the identified region, and generates the first magnified image 403 by projecting the generated three dimensional magnified image data onto the projection plane. The magnification of the three dimensional magnified image data may be a preset magnification or the image processor 101 may inquire the user after designating the position.

Next, the image generator 140 identifies the position of the magnified image 341 generated from the magnified microscope image data at each of the position designated by the first display microscope image 401 and the position identified by the second display microscope image 402. Since the first microscope image data and the second microscope image data have already been aligned at the same size, orientation and position by the image corresponding unit 160, the image generator 140 identifies the position same as the position in the first display microscope image 401 as the corresponding position in the second display microscope image 402.

Next, in the three dimensional microscope image data 310 which is the basis of the second display microscope image 402, the image generator 140 identifies a circular region having the same radius as that in the case of the first display microscope image 401, and identifies a region. Further, the image generator 140 generates the three dimensional magnified image data 340 with the same magnification as that described above after generating the three dimensional magnified image data. Further, the second magnified image 404 is generated by projecting the generated three dimensional magnified image data onto the projection plane.

Figure 28:
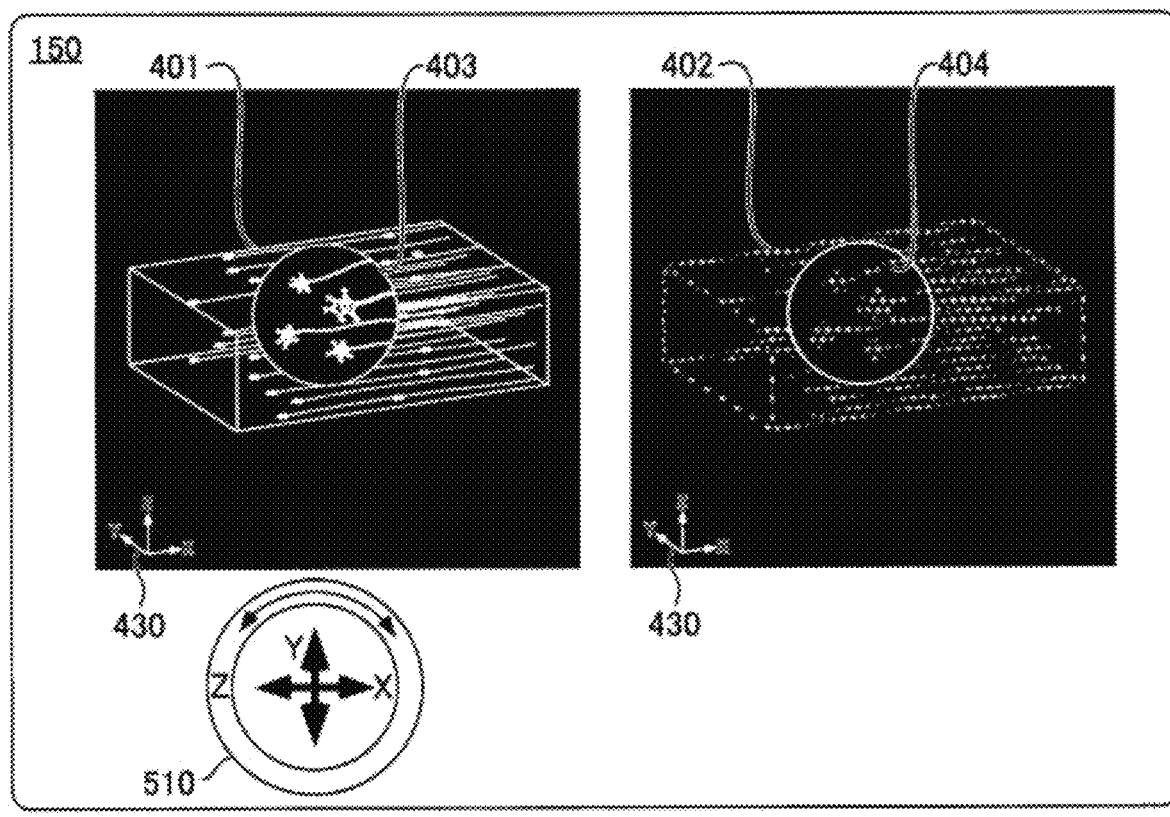
FIG. 28 is a diagram illustrating an image displayed on the display 150.

FIG. 28 is a diagram illustrating an image displayed on the display 150 after the aforementioned series of processing is completed. The first display microscope image 401 on which the first magnified image 403 is superimposed and the second display microscope image 402 on which the second magnified image 404 is superimposed are displayed side by side on the display 150. Here, the center of the first magnified image 403 coincides with the position designated with respect to the first display microscope image 401.

Therefore, the first magnified image 403 displays the surroundings of the designated position of the first display microscope image 401 such that it is magnified and observed with a magnifying glass. Therefore, the user can observe the first magnified image magnified with respect to the region that the user himself focuses while overlooking the whole with the first display microscope image 401. As a result, an intuitive observation of the microscope image can be performed.

In addition, the image generator 140 displays the second magnified image 404 by superimposing it on the second display microscope image 402. The center of the second magnified image 404 corresponds to the position designated with respect to the first display microscope image 401. Therefore, the second magnified image 404 displays the surroundings of the position corresponding to the first magnified image 403 in the second display microscope image 402 such that it is magnified and observed with the magnifying glass, thus the user can perform an intuitive observation of the microscope image while overlooking the entire second display microscope image 402.

Further, the first display microscope image 401 and the second display microscope image 402 are displayed in advance in accordance with the size, orientation and position of the image. In addition, the first magnified image 403 and the second magnified image 404 are magnified at the same magnification with respect to the first display microscope image 401 and the second display microscope image 402 being displayed, respectively.

As a result, even when the first display microscope image 401 and the second display microscope image 402 are captured with different magnifications or orientations, the comparative observation of the entire images of the first display microscope image 401 and the second display microscope image 402 can be easily performed. Further, it is possible to easily perform the comparative observation with respect to the region that the user is focused on in the first display microscope image 401 and the second display microscope image 402.

Further, the user can observe the first magnified image 403 and the second magnified image 404 generated according to the first magnified image 403 in juxtaposition by designating the position within either the first display microscope image 401 or the second display microscope image 402. Therefore, the user's operating procedure in a case where a comparative observation of the first display microscope image 401 and the second display microscope image 402 is simplified, and the work efficiency of the comparative observation is improved.

Note that, in the aforementioned example, the first magnified image 403 and the second magnified image 404 are overlapped on the first display microscope image 401 and the second display microscope image 402, respectively. In addition, the centers of the first magnified image 403 and the second magnified image 404 are displayed to coincide with the positions designated in the first display microscope image 401 and the second display microscope image 402.

However, the layout of the display is not limited to the aforementioned one. For example, the image generator 140 may display the first display microscope image 401 and the first magnified image 403 on the display 150 in juxtaposition without overlapping each other. In addition, the image generator 140 may display the first magnified image 403 on the display 150 singularly. Further, the image generator 140 may display and arrange the center of the first magnified image 403 at a position different from the designated position in the first display microscope image 401 by the user.

Similarly, regarding the second display microscope image 402 and the second magnified image 404, the layout of the display is not limited to the aforementioned one. For example, the image generator 140 may display the second display microscope image 402 and the second magnified image 404 on the display 150 in juxtaposition without overlapping each other. In addition, the image generator 140 may display the second magnified image 404 on the display 150 singularly. Further, the image generator 140 may display and arrange the center of the second magnified image 404 at a position different from the designated position in the second display microscope image 402 by the user.

Note that, the image generator 140 may display at least one of the first magnified image 403 and the first display microscope image 401, and the second magnified image 404 and the second display microscope image 402 on the device 150 in juxtaposition without overlapping it. In addition, the image generator 140 may display at least one of the first magnified image 403 and the second magnified image 404 singularly on the display 150 without displaying at least one of the first display microscope image 401 and the second display microscope image 402 on the display 150. In either case, since at least one of the first magnified image 403 and the second magnified image 404 of the region including the designated position is displayed on the display 150 by the user, the designated region can be observed in detail, and the observation of the three dimensional microscope images becomes easy.

In addition, the image generator 140 may execute the image processing in which changes the brightness and color of the first display microscope image 401, the second display microscope image 402, the first magnified image 403, and the second magnified image 404 in accordance with whether the data of the first magnified image and the data of the second magnified image are positioned on the front side or the back side. In this case, for example, the portion positioned on the front side is made brighter or more red in the three dimensional microscope image data 310 and the three dimensional magnified image data 340, and the portion positioned on the back side is made darker or more blue in the three dimensional microscope image data 310 and the three dimensional magnified image data 340. As a result, the sense of depth of the first display microscope image 401, the second display microscope image 402, the first magnified image 403, and the second magnified image 404 is emphasized, such that the three dimensional microscope image is easier to observe.

Note that, in any of the embodiments and the modifications described above, the image generator 140 may change the shape and size of the region indicated by the three dimensional magnified image data 340. Here, the shape includes a three dimensional diagram, for example, a sphere, a cone or a polygonal pyramid, a cylinder or a polygonal prism, a polyhedron and the like. For example, including changing the shape of the region indicated by the three dimensional magnified image data 340 from a sphere to a disc or a lens, or decreasing the diameter of the sphere. As a result, in a case where projecting onto the projection plane 342, the number of hidden objects positioned inside the three dimensional magnified image data 340 is reduced which make it easy to observe the inside of the three dimensional magnified image data 340. Therefore, the observation of the three dimensional images by the microscope becomes easy.

In addition, in any of the aforementioned embodiments and modifications, the accepting unit 130 accepts designation of at least a part of the three dimensional microscope image data 310 by accepting designation of the position of the microscope image or the three-dimensional three dimensional image. Instead, the accepting unit 130 may accept designation of at least a part of the three dimensional microscope image data 310 by accepting designation of a range of the microscope image or the three-dimensional three dimensional image. In this case, the accepting unit 130 accepts an operation of dragging and releasing the mouse to the microscope image or the three-dimensional three dimensional image and may accept the region of the sphere whose radius is the position released with start position of the drag as the center or designation of a region of a cube whose diagonal vertex is the start position and the release position of the drag.

In addition, in any of the embodiments and modifications described above, the image generator 140 may display the magnified image 341 and the display microscope image 321 on the display 150 in juxtaposition without superimposing them. In addition, the image generator 140 may display the magnified image 341 on the display 150 singularly without displaying the display microscope image 321 on the display 150. In either case, since the magnified image 341 of the region including the designated position is displayed on the display 150 by the user, the designated region can be observed in detail, and the observation of the three dimensional microscope images becomes easy.

In addition, in any of the embodiments and modifications described above, the image generator 140 may perform intensity conversion that distributes intensity values in a particular range in the magnified image 341 that the display 150 is caused to output and display. For example, in a case where the intensity value in the magnified image 341 (in other words, the intensity value of each pixel of the magnified image 341) is concentrated and distributed in the lower (darker) one of 256 gradations, the image generator 140 performs the conversion of the intensity such that the distribution spreads over the entire 256 gradations. Specifically, the intensity of each pixel is converted such that the intensity value of a pixel having a high intensity value is higher (brighter) among the intensity values of each pixel of the magnified image 341. On the other hand, for example, in a case where the intensity value in the magnified image 341 (in other words, the intensity value of each pixel of the magnified image 341) is concentrated and distributed in the higher (brighter) one of the 256 gradations, the image generator 140 converts the intensity of each pixel such that the intensity value of a pixel having a lower intensity value is lower (darker) among the pixels of the magnified image 341, such that the distribution spreads over the entire 256 gradations. As a result, a difference in intensity that has not been seen in the magnified image 341 appears, and an image of a fine structure of the specimen can be observed. In this case, a known look-up table and the like describing the relationship between the intensity value before conversion and the intensity value after conversion is used.

In addition, in any of the embodiments and modifications described above, the image generator 140 may perform the image processing in which the brightness and color of the display microscope image 321 and the magnified image 341 are changed between the image positioned on the front side in the three dimensional microscope image 310 and the three dimensional magnified image 340 and the image positioned on the back side. In this case, for example, in the three dimensional microscope image 310 and the three dimensional magnified image 340, the image positioned closer to the front side is made brighter and the image positioned further in the back side is made darker. In addition, in the three dimensional microscope image data 310 and the three dimensional magnified image data 340, the image positioned closer to the front side may be made redder, and the portion positioned further in the back may be made more blue. As a result, the sense of depth of the display microscope image 321 and the magnified image 341 is emphasized, and the three dimensional microscope image is easier to observe. Therefore, the observation of the three dimensional microscope magnified images becomes easier.

Each operation of the image processor 101 may be provided as a computer program and realized by installing the computer program.

Although the present disclosure has been described with reference to the embodiments, the technical scope of the present disclosure is not limited to the scope described in the aforementioned embodiments. It is obvious to a person skilled in the art that various modifications or improvements can be added to the above embodiments. It is obvious from the description of the scope of the claims that the embodiments added with such modifications or improvements can be included in the technical scope of the present disclosure.

The sequence of execution of each process, such as operation, procedure, step, and stage and the like in the device, system, program, and method illustrated in the claims, the description, and the diagrams is not particularly stated as "before", "prior" and the like, and it should be noted that they can be realized in any order as long as the output of the previous processing is not used in the subsequent processing. Regarding the operation flow in the claims, description, and diagrams, it means that it is not essential to be preform in this order even if they are described using "first", "next", and the like for convenience.

The invention claimed is:

1. A computer comprising:
   a processor programmed to:
   accept designation of at least a part of a three dimensional image of a microscope; and
   generate image data for displaying, on a display, a first magnified image which corresponds to the designated part of the three dimensional image, wherein
   the processor is programmed to generate the first magnified image from three dimensional image data corresponding to the three dimensional image by using one of a projection and a rendering,
   the processor is programmed to accept a designation of a change of an observation direction of the three dimensional image and a designation of a change of an observation direction of the first magnified image, and
   the processor is programmed to output image data, for displaying on the display, of the three dimensional image such that an orientation of the three dimensional image is changed based on the designation of the change of the observation direction of the three dimensional image, and output image data, for displaying on the display, of the first magnified image such that an orientation of the first magnified image is changed based on the designation of the change of the observation direction of the first magnified image.

2. The computer according to claim 1, wherein
   the processor is programmed to generate image data for displaying, on the display, a second magnified image which corresponds to the designated part of the three dimensional image and which is different from the first magnified image, the processor is programmed to generate the second magnified image from the three dimensional image data corresponding to the three dimensional image by using one of the projection and the rendering, the first magnified image is different from the second magnified image in the projection or the rendering, and the first magnified image is different from the second magnified image in an observation direction of the three dimensional image.

3. The computer according to claim 2, wherein
the processor outputs, to the display, image data of the first magnified image and the second magnified image such that the first magnified image and the second magnified image are displayed on the display at different times.

4. The computer according to claim 3, wherein
the processor generates image data for displaying, on the display, a first microscope image of which an area in the three dimensional image is wider than an area, of the first magnified image, in the three dimensional image, and a second microscope image of which an area in the three dimensional image is wider than an area, of the second magnified image, in the three dimensional image.

5. The computer according to claim 4, wherein
the processor generates image data for displaying, on the display, an image in which the first magnified image and the first microscope image are superimposed, and an image in which the second magnified image and the second microscope image are superimposed.

6. The computer according to claim 2, wherein
the processor generates image data for displaying, on the display, a reference image,
the processor accepts designation of at least a part of the reference image, and
the processor generates image data for displaying, on the display, the first magnified image which corresponds to the part of the three dimensional image corresponding to the designated part of the reference image and the second magnified image which corresponds to the designated part of the three dimensional image and which is different from the first magnified image.

7. The computer according to claim 2, wherein
the processor accepts input of information regarding a route for displaying a magnified image, and
the processor outputs, to the display, image data of the first magnified image and the second magnified image such that the first magnified image and the second magnified image are displayed on the display at different times along the route.

8. The computer according to claim 2, wherein
the processor accepts designation of a change of the observation direction of the three dimensional image, and
the processor outputs image data of the first magnified image and the second magnified image such that a display image displayed on the display is changed from the first magnified image to the second magnified image based on the designation of the change of the observation direction.

9. The computer according to claim 8, wherein
the processor generates a three dimensional magnified image obtained by magnifying the designated part of the three dimensional image, and the processor generates image data of the first magnified image and image data of the second magnified image, such that an orientation of the three dimensional magnified image is changed with respect to an arbitrary projection plane, and that the three dimensional magnified image is projected on the projection plane based on the designation of the change of the observation direction.

10. The computer according to claim 1, wherein
the processor generates image data for displaying, on the display, a microscope image of at least a part of the three dimensional image of the microscope, and
the processor accepts designation of at least a part of the microscope image displayed on the display.

11. The computer according to claim 10, wherein
the microscope image includes microscope images of at least two planes which are not parallel to each other in the three dimensional microscope image, and
the processor accepts designation of at least a part of each of the microscope images of the two planes displayed on the display.

12. The computer according to claim 10, wherein
the microscope image includes microscope images of a plurality of planes which are parallel to each other in the three dimensional microscope image, and
the processor accepts selection of a particular microscope image from the microscope images of the plurality of planes displayed on the display and accepts designation of at least a part of the particular microscope image.

13. The computer according to claim 10, wherein
the microscope image includes the three dimensional image of the microscope based on the three dimensional microscope image data, and
the processor accepts designation of a position in at least a part of the three dimensional microscope image displayed on the display.

14. The computer according to claim 10, wherein
the microscope image includes a projection image obtained by projecting the three dimensional image on an arbitrary plane, and
the processor accepts designation of at least a part of the projection image displayed on the display.

15. The computer according to claim 1, wherein
the processor generates image data for displaying, on the display, a position reference image indicating a position, in the three dimensional image, accepted by the processor.

16. The computer according to claim 4, wherein
the processor accepts input of a threshold regarding a pixel value of a magnified image, and
the processor generates a magnified image to be displayed under a different display condition based on the threshold.

17. The computer according to claim 4, wherein
the processor generates image data for displaying, on the display, a magnified image of an area of a second three dimensional image, the area of the second three dimensional image corresponding to the designated part of the three dimensional image, the second three dimensional image being obtained by a different microscopy that is different from the microscope.

18. A microscope system comprising:
a computer according to claim 1;
a microscope configured to output microscope image data to the computer; and
a display configured to display an image based on the microscope image data output from the computer.

19. An image processing method comprising:
accepting designation of at least a part of a three dimensional image of a microscope;
generating image data for displaying, on a display, a first magnified image which corresponds to the designated part of the three dimensional image, wherein
the first magnified image is generated from three dimensional image data corresponding to the three dimensional image by using one of a projection and a rendering;
accepting a designation of a change of an observation direction of the three dimensional image and a designation of a change of an observation direction of the first magnified image; and
outputting image data, for displaying on the display, of the three dimensional image such that an orientation of the three dimensional image is changed based on the designation of the change of the observation direction of the three dimensional image, and outputting image data, for displaying on the display, of the first magnified image such that an orientation of the first magnified image is changed based on the designation of the change of the observation direction of the first magnified image.

20. The image processing method according to claim 19, further comprising
generating image data for displaying, on the display, a second magnified image which corresponds to the designated part of the three dimensional image and which is different from the first magnified image, wherein
the second magnified image is generated from the three dimensional image data corresponding to the three dimensional image by using one of the projection and the rendering,
the first magnified image is different from the second magnified image in the projection or the rendering, and
the first magnified image is different from the second magnified image in an observation direction of the three dimensional image.

21. The image processing method according to claim 20, wherein
generating the image data includes outputting, to the display, image data of the first magnified image and the second magnified image such that the first magnified image and the second magnified image are displayed on the display at different times.

22. The image processing method according to claim 21, wherein
generating the image data includes: generating image data for displaying, on the display, a first microscope image of which an area in the three dimensional image is wider than an area, of the first magnified image, in the three dimensional image, and a second microscope image of which an area in the three dimensional image is wider than an area, of the second magnified image, in the three dimensional image.

23. The image processing method according to claim 20, wherein
generating the image data includes generating image data for displaying, on the display, an image in which the first magnified image and the first microscope image are superimposed, and an image in which the second magnified image and the second microscope image are superimposed.

24. The image processing method according to claim 20, wherein
accepting the designation includes accepting designation of a change of the observation direction of the three dimensional image, and
generating the image data includes outputting image data of the first magnified image and the second magnified image such that a display image displayed on the display is changed from the first magnified image to the second magnified image based on the designation of the change of the observation direction.

25. The image processing method according to claim 24, wherein
generating the image data includes generating a three dimensional magnified image obtained by magnifying the designated part of the three dimensional image, and
generating the image data includes generating image data of the first magnified image and image data of the second magnified image, such that an orientation of the three dimensional magnified image is changed with respect to an arbitrary projection plane, and that the three dimensional magnified image is projected on the projection plane based on the designation of the change of the observation direction.

26. The image processing method according to claim 20, further comprising:
generating image data for displaying, on the display, a reference image, wherein
accepting the designation includes accepting designation of at least a part of the reference image, and
generating image data for displaying, on the display, the first magnified image which corresponds to the part of the three dimensional image corresponding to the designated part of the reference image and the second magnified image which corresponds to the designated part of the three dimensional image and which is different from the first magnified image.

27. The image processing method according to claim 19, further comprising:
generating image data for displaying, on the display, a microscope image of at least a part of the three dimensional image of the microscope, wherein
accepting the designation includes accepting designation of at least a part of the microscope image.

28. The image processing method according to claim 27, wherein
the microscope image includes microscope images of at least two planes which are not parallel to each other in the three dimensional microscope image based on the three dimensional microscope image data, and
accepting the designation includes accepting designation of at least a part of each of the microscope images of the two planes.

29. The image processing method according to claim 27, wherein
the microscope image includes microscope images of a plurality of planes which are parallel to each other in the three dimensional microscope image based on the three dimensional microscope image data, and
accepting the designation includes accepting selection of a particular microscope image from the microscope images of the plurality of planes and accepting designation of at least a part of the particular microscope image.

30. The image processing method according to claim 27, wherein
the microscope image includes the three dimensional image of the microscope.

31. The image processing method according to claim 27, wherein
the microscope image includes a projection image obtained by projecting the three dimensional image on an arbitrary plane, and
accepting the designation includes accepting designation of at least a part of the projection image.

32. A non-transitory computer readable medium storing a computer program configured to cause a computer to execute:
accepting designation of at least a part of a three dimensional image of a microscope;
generating image data for displaying, on a display, a first magnified image which corresponds to the designated part of the three dimensional image, wherein
the first magnified image is generated from three dimensional image data corresponding to the three dimensional image by using one of a projection and a rendering;
accepting a designation of a change of an observation direction of the three dimensional image and a designation of a change of an observation direction of the first magnified image; and
outputting image data, for displaying on the display, of the three dimensional image such that an orientation of the three dimensional image is changed based on the designation of the change of the observation direction of the three dimensional image, and outputting image data, for displaying on the display, of the first magnified image such that an orientation of the first magnified image is changed based on the designation of the change of the observation direction of the first magnified image.

* * * * *